(12) United States Patent
Refseth et al.

(10) Patent No.: US 7,964,364 B2
(45) Date of Patent: Jun. 21, 2011

(54) CELL ISOLATION METHOD

(75) Inventors: Unn Hilde Refseth, Oslo (NO); Tone Kolpus, Oslo (NO)

(73) Assignee: Nordiag ASA, Oslo (NO)

( * ) Notice: Subject to any disclaimer, the term of this patent is extended or adjusted under 35 U.S.C. 154(b) by 504 days.

(21) Appl. No.: 10/169,898

(22) PCT Filed: Jan. 22, 2001

(86) PCT No.: PCT/GB01/00240
§ 371 (c)(1),
(2), (4) Date: Nov. 5, 2002

(87) PCT Pub. No.: WO01/53525
PCT Pub. Date: Jul. 26, 2001

(65) Prior Publication Data
US 2003/0153028 A1    Aug. 14, 2003

(30) Foreign Application Priority Data

Jan. 21, 2000 (GB) .................... 0001450.6

(51) Int. Cl.
*G01N 33/53* (2006.01)
(52) U.S. Cl. .................. 435/7.2; 435/7.1; 436/518
(58) Field of Classification Search .......... 435/7.1, 435/7.2, 287.1, 7.32, 177; 436/526, 806, 436/518
See application file for complete search history.

(56) References Cited

U.S. PATENT DOCUMENTS

| | | | |
|---|---|---|---|
| 4,111,838 A * | 9/1978 | Schaeffer et al. ........... 502/7 |
| 4,336,173 A | 6/1982 | Ugelstad |
| 4,459,378 A | 7/1984 | Ugelstad |
| 4,543,328 A | 9/1985 | Keller et al. |
| 4,654,267 A | 3/1987 | Ugelstad et al. |
| 4,689,294 A * | 8/1987 | Boguslawski et al. ......... 435/6 |
| 4,719,182 A * | 1/1988 | Burdick et al. ............ 436/501 |
| 4,791,063 A * | 12/1988 | Hou et al. ................ 435/243 |
| 4,929,452 A * | 5/1990 | Hamdy .................... 426/11 |
| 4,935,147 A | 6/1990 | Ullman et al. |
| 4,978,616 A * | 12/1990 | Dean et al. ............... 435/70.3 |
| 5,034,314 A * | 7/1991 | Geiger et al. ............... 435/6 |
| 5,270,189 A * | 12/1993 | Scott ..................... 435/139 |
| 5,486,457 A * | 1/1996 | Butler et al. .............. 435/7.2 |
| 5,696,000 A | 12/1997 | Krivan et al. |
| 5,773,223 A * | 6/1998 | Shyamala et al. .......... 435/7.2 |
| 6,362,010 B1 * | 3/2002 | Magnani ................. 436/518 |

FOREIGN PATENT DOCUMENTS

| | | |
|---|---|---|
| CA | 2227608 | 2/1997 |
| EP | 0 389 063 A2 | 9/1990 |
| EP | 1118676 A2 | 7/2001 |
| WO | WO8303920 | 11/1983 |
| WO | WO-8903674 * | 5/1989 |
| WO | WO91/06007 | 5/1991 |
| WO | WO91/12079 | 8/1991 |
| WO | WO96/18731 | 6/1996 |
| WO | WO98/51693 | 11/1998 |

OTHER PUBLICATIONS

Griegel et al. (Anticancer Research 1989 vol. 9, p. 723).*
Sanchez et al. (APMIS 1990 vol. 98, p. 353).*
Lechat et al. J. Appl. Phycology 1997 vol. 9, p. 565-572.*
Gratta et al. Phys Med. Biol 1995 vol. 40, p. 671-681.*
Abramson et al. (1993) Current Opinion in Biotechnology 4:41-47.
Bastin et al. (1995) Gene 164:17-23.
Castellanos et al. (1998) Current Microbiology 36:241-244.
Hirmo et al. (1997) Lectins, Biology, Biochemistry, Clinical Biochemistry, vol. 12, van Driessche et al., eds, TEXTOP, Hellerup, Denmark.
Leusch et al. (1991) Infection and Immunity 59:2051-2057.
Pan et al. (1997) Infection and Immunity 65:4199-4206.
Sanchez et al. (1990) APMIS 98:353-357.
Sasmal et al. (1999) FEMS Immunology and Medical Microbiology 23:221-227.
Skjerve et al. (1990) Applied and Environmental Microbiology 56:3478-3481.
Syvanen et al. (1990) Genomics 8:684-692.
Vadivelu et al. (1995) J. Med. Microbiol. 42:171-174.
Wahlberg et al. (1990) Molecular and Cellular Probes 4:285-297.
Watnick et al. (1999) Journal of Bacteriology 181:3606-3609.
Zareba et al. (1997) Current Microbiology 34:6-11.

* cited by examiner

*Primary Examiner* — Jacob Cheu
(74) *Attorney, Agent, or Firm* — Fox Rothschild LLP

(57) ABSTRACT

The present invention relates to a method of isolating cells from a sample which method comprises binding said cells to a solid support by means of a non-specific ligand immobilised on said solid support, particularly to a method of isolating microorganisms from a sample. Preferred ligands for use in such methods include carbohydrates and derivatives thereof. Also described is a kit for isolating microorganisms from a sample comprising: (a) a solid support having immobilised thereon a ligand which is capable of non-specific binding to microorganisms; (b) means for binding microorganisms to said solid support; optionally (c) means for lysing said cells; and optionally (d) means for binding nucleic acid released from said lysed cells to a solid support.

20 Claims, 11 Drawing Sheets

CELL ISOLATION METHOD

The present invention relates to a method of isolating microorganisms present in a sample, in particular to a method of isolating bacteria present in a sample.

The majority of current techniques which seek to analyse samples qualitatively and quantitatively for the presence of microorganisms are directed to identification of a specific microorganism, e.g. a pathogen. Immunomagnetic separation of strains of *Listeria* and *Salmonella* from food and clinical samples has been described (see for example Skjerve et al. Appl. *Environ. Microbiol.* 1990, 3478-3481). Such techniques rely upon the use of ligands, generally antibodies, specific for the microorganism concerned. As it relies upon the use of specific ligands, immunomagnetic separation is applicably only in situations where a particular microorganism is sought to be identified and not where a general screen for microorganisms which may be present is desired. Immunomagnetic separation will not readily pick up unsuspected microorganisms.

There are situations, for example when analysing environmental samples, such as water samples where it may be desirable to obtain a full picture of the different species of microorganisms present or an estimate of the total concentration of microorganisms. Limits may be placed on the total amount of bacteria which may be present in the water supply, which is independent of concerns about the presence of particular bacteria. Identification of broad classes of microorganisms e.g. in a river or lake may provide useful information about the state of that body of water, levels of nutrients, run-off of agrochemicals etc.

If a general method for isolating microorganisms from a sample can be provided, identification of the particular microorganisms present can then conveniently be performed in a subsequent step. Nucleic acid based assays could conveniently be used to identify specific microorganisms.

Methods currently used to obtain estimates of the total amount of microorganisms present in a sample or to isolate the microorganisms from the sample for further analysis rely on rather crude separation techniques involving filtration and/or centrifugation and culturing on agar plates. Determination of total bacterial concentration may be performed by flow cytometry or filtration and culturing on a general medium in a petri dish for example. These methods may take several days and are rather complex and imprecise. Particular problems have been observed with conventional methods used to analyse food samples as these contain a lot of solid material (clumps and fatty particles) which tend to block filters and after centrifugation produce a pellet where the bacteria are packed and not available for lysing or binding to antibodies.

There is therefore a need for a method which is able to isolate a number of different species of microorganism from a sample, preferably in a single step, which is quick and convenient to perform.

The present invention addresses these requirements and thus according to one aspect of the present invention is provided a method of isolating microorganisms from a sample which method comprises binding said microorganisms to a solid support by means of a non-specific ligand immobilised on said solid support.

The present invention therefore provides, through utilisation of the interactions between non-specific ligands attached to solid supports and binding partners for said ligands (receptors) found on the surface of microorganisms, a general separation method which allows for the capture of broad classes of microorganisms. As the essence of the present invention is the non-specific interaction between the immobilised ligand and microorganisms, when reference is made herein to "isolating microorganisms" it is intended to describe the isolation of microorganisms in a non-species and non-genus specific manner. In other words, the immobilised ligand is able to bind to several genera of microorganism, at least 2 different genera, preferably 3 or more, more preferably at least 5 or 7 different genera, most preferably at least 10 or even 14 or more different genera.

The present invention thus provides a general method of isolating microorganisms, especially bacteria, from the other components in a sample. The method is 'general' in the sense that one bacterial species is not targetted but a gross separation system is achieved to obtain information about the total microorganism population or to facilitate a second step through which species specific information is obtained, e.g. at the nucleic acid level using species specific probes.

The microorganisms are "isolated" in that they are bound to the solid support and then may be separated from the remainder of the sample by removing the solid support with microorganisms bound thereto or by removing, e.g. by running off, the remainder of the sample. Where the solid support is magnetic, manipulation of the support/microorganism complex is especially convenient.

The method of the present invention may be used to isolate a wide variety of microorganisms including all those microorganisms which can bind to eukaryotic cells, including the protists, algae, protozoa and fungi as well as mycoplasmas and all bacteria and viruses. The methods of the invention may be used in the isolation of eukaryotic parasites, particularly those which are able to bind the complex polysaccharides found on human cells (or other host organisms). Such eukaryotic parasites include *Cryptosporidium, Entamoeba histolytica* and the malaria parasite. Therefore reference herein to "microorganisms" should be taken to include such parasites.

The methods of the invention are particularly suitable for isolating bacteria. Bacterial classification is a complex and ever changing science but 'true' bacteria (eubacteria) may be divided into a number of Parts (Bergey's Manual of Determinative Biology) e.g. phototrophic bacteria, gliding bacteria, sheathed bacteria and Gram-Positive cocci. Each Part may in turn be divided into one or more orders with families and genera within that order. Bacteria from more than one genus, family or order or even Part may be isolated using the methods of the present invention. Effective separation from a sample of bacteria from some or all of the following families and genera of bacteria may be achieved using the present methods: *Aeromonas, Bacillus, Campylobacter, Citrobacter, Clostridium, Enterobacter, Escherichia* (pathogen and non-pathogen), *Hafnia, Klebsiella, Listeria, Proteus, Salmonella, Shewanella, Serratia, Shigella, Vibrio, Yersinia, Morganella, Photobacterium, Streptococcus, Lactococcus, Staphylococcus, Enterococcus, Leuconostoc, Pediococcus, Lactobacillus, Brochothrix.*

The method may be used to isolate simultaneously bacteria and other types of microorganism, e.g. algae, protozoa, fungi or viruses.

In certain circumstances, the sample may only contain a limited number of types of bacteria and the method may only result in a few species of bacteria, or even only one or two species, being bound and thus isolated from the sample. Such a method is still not a specific isolation method as the immobilised ligand is capable of binding to a wide variety of bacteria even if the available bacterial populations are rather limited.

The fact that a specific solid-support-ligand complex does not need to be selected in order to perform a given isolation method provides a significant advantage in terms of flexibility and cost as one solid support with attached ligand can be used in a wide variety of isolation/separation methods. It is therefore the general binding capabilities of the solid support which is particularly advantageous.

Preferably, the methods of the invention will result in a large proportion of the microorganisms (e.g. bacteria) present in the sample being isolated, both in terms of the proportion of all bacterial cells present and the proportion of types of bacteria. Thus, preferably at least 30%, more preferably at least 50%, most preferably at least 70 or 80% of the microorganisms in the sample will be bound to be solid support. Of course, the percentage of microorganisms in the sample which are bound will depend on the amount of solid support added to the sample and the ratio of ligand to microorganism. It is assumed for the above percentages that there is an excess of solid support and ligand present in the mixture.

Alternatively viewed, representatives from at least 20% of the different (e.g. bacterial) species present will preferably be isolated, more preferably representatives from at least 30 or 40%, most preferably at least 50%, particularly at least 60 or 70% or even at least 80% of the different (e.g. bacterial) species present will be bound to the solid support.

The 'non-specific' ligand will be one which, as discussed above, is capable of binding to more than one type of microorganism and/or bacterial genus, preferably to more than 2 or 3, more preferably to more than 5 or 7 e.g. more than 10 or 14 different genera. There is an interaction between the ligand and its binding partner(s) on the surface of the microorganism which is responsible for binding, it is not the case that there is simply a general attraction or association between the cells and the solid support, as may be the case when cells bind by precipitation. The non-specific character of the ligand refers not to the fact that it is capable of binding or associating indiscriminately with moieties on the surface of microorganisms but that its binding partner(s) is not specific to a certain type or species of microorganism. The ligand can therefore be considered to be a general binding ligand.

As suitable binding partners are relatively widely found amongst different microorganisms, in particular amongst different genera of bacteria, a rather general and thus non-specific isolation method is provided. Thus the ligand, while it may have one or more specific binding partners, is 'non-specific' in the sense that it is capable of binding to a variety of different bacteria, all of which carry a suitable binding partner. Although not wishing to be bound by theory, it seems that a variety of different binding partners, which are themselves typically species specific, are able to bind the same ligand thus providing a separation method which is not species specific. Species specific lectins are able to provide a non-species specific separation system with carbohydrate based ligands.

The binding partners are typically proteins on the surface of the microorganisms and may vary from species to species. Not a great deal is known about the binding partners but the inventors have nevertheless been able to identify suitable ligands for use in the methods of the invention.

The ligand is non-proteinaceous and thus antibodies and derivatives and fragments thereof are excluded. In contrast to the non-specific ligands of the present method, such proteinaceous ligands are capable of very specific (i.e. genera, in particular species specific) interactions e.g. with proteins on cell surfaces.

Preferred ligands are carbohydrates including monosaccharides, oligosaccharides (including disaccharides and trisaccharides) and polysaccharides. Suitable monosaccharides include hexoses and pentoses in pyranose and furanose form where appropriate, as well as sugar derivatives such as aldonic and uronic acids, deoxy or amino sugars, sulfated sugars, and sugar alcohols. Suitable monosaccharides may be exemplified by mannose (e.g. D-mannose), galactose (e.g. D-galactose), glucose (e.g. D-glucose), fructose, fucose (e.g. L-fucose), N-acetyl-glucosamine, N-acetyl-galactosamine, rhamnose, galactosamine, glucosamine (e.g. D-glucosamine), galacturonic acid, glucuronic acid, N-acetylneuraminic acid, methyl D-mannopyranoside (mannoside), $\alpha$-methyl-glucoside, galactoside, ribose, xylose, arabinose, saccharate, mannitol, sorbitol, inositol, glycerol and derivatives of these monomers. Of these, mannose, galactose and fucose are preferred.

Particularly preferred are oligosaccharides and polysaccharides which are polymers of monosaccharide monomers, for example polymers incorporating the monosaccharide monomers discussed above.

Oligosaccharides comprise 2 to 12, preferably 4 to 8, covalently linked monosaccharide units which may be the same or different and which may be linear or branched, preferably branched, e.g. oligomannosyl having 2 to 6 units, maltose, sucrose, trehalose, cellobiose, and salicin, particularly maltose. A method for production of oligosaccharides is described in Pan et al. Infection and Immunity (1997), 4199-4206.

Polysaccharides comprise 13 or more covalently linked monosaccharide units which may be the same or different and which may be linear or branched, preferably branched. Suitable polysaccharides will be rich in mannose, galactose, glucose, fructose or uronic acids e.g. galactomannan polysaccharide (referred to herein as GUM or GUM 1) (Sigma G-0753) which is believed to be a straight chain polymer of mannose with one galactose branch on every fourth mannose.

Polysaccharides which are made up of mannose and galactose sub-units are a preferred type of ligand and a further example is guar which has a $\beta$ 1,4 linked linear mannose backbone chain with a galactose side unit on approximately every other unit in a 1,6 $\alpha$ linkage. The mannose to galactose ratio is about 1.8:1 to about 2:1; the guar used in the experiments described herein is from Sigma, catalogue reference number G1429.

Further polysaccharides include Gum Arabic (Sigma G 9752) believed to be a branched polymer of galactose, rhamnose, arabionse and glucuronic acid and Gum Karaya (Sigma G 0503) believed to be a partially acetylated polymer of galactose, rhamnose and glucuronic acid, as well as the homo-polysaccharide mannan, made up of mannose units.

Sugar derivatives which are suitable ligands include heparin, heparan sulphate, dextran sulphate and carrageenan (various forms). Sulphated sugars are a preferred class of sugar derivatives.

The inventors have found that ligands based on molecules which are nutrients for microorganisms, such as carbohydrates, provide suitable separation means. It was an aim of the present method to provide an isolation system which as well as utilising receptor/ligand interactions took advantage of the proactive response of bacteria to the presence of nutrients in the media in order to enhance capture of microorganisms. Further nutrients for microorganisms which may thus be used as non-specific ligands according to the methods of the present invention include vitamins such as nicotinic acid, riboflavin, thiamin, pyridoxine, pantothenic acid, folic acid, biotin and cobamide and iron-chelating molecules/compounds such as hemin, lactoferrin, transferrin, hemoglobin and siderophores such as aerobactin, ferrichrome (Sigma F8014), ferrienterochelin, enterobactin and ferrixanine.

A solid support having immobilised thereon a ligand which is capable of binding to cells (e.g. microorganisms) in a non-specific manner thus constitutes a further aspect of the present invention. 'Non-specific' is as defined above (i.e. not cell type or species specific but still relying on interactions with a binding partner) and suitable ligands are described herein with reference to the methods.

In the context of investigating the fucose-sensitive and mannose-sensitive hemagglutination of the bacteria *Vibrio cholerae*, L-fucose and D-mannose have been covalently attached to agarose beads (Sanchez et al. APMIS (1990) 98 353-357) and thus these solid support-ligand complexes are not included within the scope of the present invention. This previous work was investigating a very specific interaction involving just one species of bacteria and is not a general bacterial isolation method. Therefore the use of these bead-ligand complexes in the context of the methods defined herein do comprise an aspect of the present invention.

The immobilised ligand will preferably be an oligo- or polysaccharide, vitamin (e.g. one required as a nutrient for microorganisms) or iron-chelating compound, polysaccharides being particularly preferred. Examples of particularly preferred ligands are discussed previously in the discussion relating to the methods.

Although as discussed herein a general separation method is provided, the inventors have found that ligands incorporating certain sugars are particularly suitable for separating certain very broad classes of microorganism. Thus, for example bacterial species present in the gut are very efficiently isolated when a mannose containing ligand is used (the ligand may be a mannose monomer or mannose incorporating polymer), bacteria which enter through the lung are very efficiently isolated using sulphated sugars as ligands and bacteria which infect the urinary tract bind to immobilised glucose (again, as a monomer or when incorporated into a polymer). The use of such ligands in methods to separate bacteria from a sample taken from the gut or lung thus constitutes further preferred aspects of the present invention.

The sample from which microorganisms may be isolated includes environmental samples such as water samples, e.g. from lakes, rivers, sewage plants and other water-treatment centers or soil samples. The methods are of particular utility in the analysis of food samples and generally in health and hygiene applications where it is desired to monitor bacterial levels, e.g. in areas where food is being prepared. Milk products for example may be analysed for listeria. Conventional techniques for bacterial isolation using immobilised antibodies have proved to be much less effective than our methods for isolating listeria using non-specific ligands, possibly due to the hydrophobic nature of the immobilised antibody. When the sample is a water sample, the ligand is preferably a nutrient for the microorganisms of interest.

Food samples may be analysed by first homogenising where necessary (if a solid sample) then mixing with a suitable incubation media (e.g. peptone water) and incubating at 37° C. overnight. Food such as cheese, ice cream, eggs, margarine, fish, shrimps, chicken, beef, pork ribs, wheat flour, rolled oats, boiled rice, pepper, vegetables such as tomato, broccoli, beans, peanuts and marzipan may be analysed in this way. The methods of the invention offer particular benefits for the analysis of food samples as these contain a lot of solid material (clumps and fatty particles) which tend to block filters and after centrifugation produce a pellet where the bacteria are packed and not available for lysing or binding to antibodies.

Samples from which microorganisms may be isolated according to the present method may be clinical samples taken from the human or animal body. Suitable samples include, whole blood and blood derived products, urine, faeces, cerebrospinal fluid or any other body fluids as well as tissue samples and samples obtained by e.g. a swab of a body cavity.

The sample may also include relatively pure or partially purified starting materials, such as semi-pure preparations obtained by other cell separation processes.

It has also been found that the solid supports and methods of the invention can be used in the non-selective isolation of eukaryotic cells from a sample. The method is 'non-selective' in that a single cell type is not targetted for isolation. At least 2, preferably 3 or more, 4 or more of even 6 or more different eukaryotic cell types will be isolated according to these methods.

Thus, in a further aspect, the present invention provides a method of isolating eukaryotic cells from a sample which method comprises binding said eukaryotic cells to a solid support by means of a non-specific ligand immobilised on said solid support. Suitable eukaryotic cells which may be separated are those which have lectins on their surface which bind to polysaccharides. Such a method may have particular utility when it is desirable to capture all types of white blood cells from a blood or blood derived sample, from bone marrow or indeed any tissue or fluid containing white blood cells. For this application particularly suitable ligands include carrageenan and derivatives thereof, sulphated polysaccharides (glycosaminoglycans) such as dextran sulphate, heparin and heparan sulphate.

According to such a method of the invention, at least B-cells and monocytes, preferably most if not all types of white blood cells can be isolated through binding to the same beads. Red blood cells are preferably not captured. This method is typically a preliminary step in a method of isolating DNA from a sample. Isolation of DNA from blood according to prior art methods is achieved by direct lysis of the sample and capture of DNA. Such a technique will lyse all cells present, whereas according to the method of the present invention, white blood cells are bound allowing an initial concentration of the cells of interest. An antibody based separation system would not allow the capture of white blood cells generally. In an analogous manner, other groups of cells can be isolated from a eukaryotic sample.

The present invention therefore provides a cell isolation method wherein the 'cell' may be eukaryotic or prokaryotic, the term 'cell' encompassing all the microorganisms previously defined.

Suitable solid supports for use in the present invention may be any of the well known supports or matrices which are currently widely used or proposed for immobilisation, separation etc. These may take the form of particles, sheets, gels, filters, membranes, fibres, capillaries, or microtitre strips, tubes, plates or wells etc.

Conveniently the support may be made of glass, silica, latex or a polymeric material. Preferred are materials presenting a high surface area for binding of the cells, and subsequently, of the nucleic acid. Such supports will generally have an irregular surface and may be for example be porous or particulate eg. particles, fibres, webs, sinters or sieves. Particulate materials eg. beads are generally preferred due to their greater binding capacity, particularly polymeric beads.

Conveniently, a particulate solid support used according to the invention will comprise spherical beads. The size of the beads is not critical, but they may for example be of the order of diameter of at least 1 and preferably at least 2 μm, and have a maximum diameter of preferably not more than 10 and more preferably not more than 6 µm. For example, beads of diameter 2.8 µm and 4.5 µm have been shown to work well.

Non-magnetic polymer beads suitable for use in the method of the invention are available from Dyno Particles AS (Lillestrøm, Norway) as well as from Qiagen, Pharmacia and Serotec.

However, to aid manipulation and separation, magnetic beads are preferred. The term "magnetic" as used herein means that the support is capable of having a magnetic moment imparted to it when placed in a magnetic field, and thus is displaceable under the action of that field. In other words, a support comprising magnetic particles may readily be removed by magnetic aggregation, which provides a quick, simple and efficient way of separating the particles following the cell and nucleic acid binding steps, and is a far less rigorous method than traditional techniques such as centrifugation which generate shear forces which may disrupt cells or degrade nucleic acids.

Thus, using the method of the invention, the magnetic particles with cells attached may be removed onto a suitable surface by application of a magnetic field eg. using a permanent magnet. It is usually sufficient to apply a magnet to the side of the vessel containing the sample mixture to aggregate the particles to the wall of the vessel and to pour away the remainder of the sample.

Especially preferred are superparamagnetic particles for example those described by Sintef in EP-A-106873, as magnetic aggregation and clumping of the particles during reaction can be avoided, thus ensuring uniform and nucleic acid extraction. The well-known magnetic particles sold by Dynal AS (Oslo, Norway) as DYNABEADS, are suited to use in the present invention.

Functionalised coated particles for use in the present invention may be prepared by modification of the beads according to U.S. Pat. Nos. 4,336,173, 4,459,378 and 4,654,267. Thus, beads, or other supports, may be prepared having different types of functionalised surface, for example positively or negatively charged, hydrophilic or hydrophobic.

The particles will preferably provide a large surface area for binding and will therefore tend to be small and possibly not smooth. The surface of the solid-support will preferably (either before or after ligand immobilisation) not be hydrophobic.

Particularly preferred particles for use as a solid support in the methods of the invention are spherical shaped polymer particles (beads) based on PVA (polyvinyl alcohol) in which a magnetic colloid has been encapsulated. These beads may be produced through suspension of a polymer phase containing magnetic colloids in a vegetable oil phase containing an emulsifier as described in CA 2,227,608. The particles, which may vary in size from 1-8 µm, preferably are available from Chemagen AG, Germany.

Appropriate buffers etc. may be used as media for the isolation to achieve conditions appropriate for binding. Conveniently, a buffer of appropriate charge, osmolarity etc. may be added to the sample prior to, simultaneously with or after contact with the solid support. PBS is a suitable cell binding buffer.

Methods for attachment of a ligand to a solid support are well known in the art. Typically, the solid support will first be activated and then reacted with the ligand, the ligand may itself have been modified slightly for covalent attachment to the solid support. In the case of the superparamagnetic beads from Chemagen which are discussed above, the polyvinyl alcohol matrix may be activated by the introduction of isocyanate functionalities via an 8 atom spacer. These activated beads (M-PVA A k2x) can then be used for the direct coupling of molecules containing amino or hydroxy functionalities. A typical coupling reaction would be as follows:

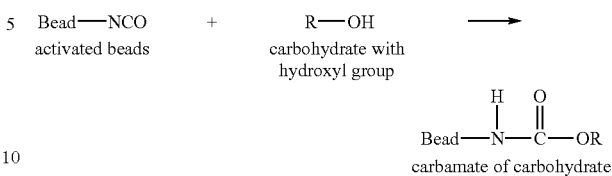

Chemagen have patents relating to the modification of their beads by coupling.

In order to investigate cell binding and where qualitative or quantitative information about specific microorganisms is required, a further identification step may be performed. The combination of a general cell separation method as described above with a species specific detection method represents a particularly preferred embodiment of the present invention.

The identity of the bound microorganisms may be investigated by analysis of the nucleic acid of the microorganisms or by other techniques known in the art such as by the use of labelled antibodies which are specific for certain types of microorganism. Conveniently, after the cells have bound to the solid support, nucleic acid from the microorganism-bead complex may be isolated and analysed, e.g. by PCR. Thus, after the microorganisms have bound to said solid support there will be a cell lysis step to release the nucleic acid from the microorganisms for subsequent analysis. The released nucleic acid may be analysed in solution but is more conveniently analysed after it has bound to a solid support, this solid support may be the same or different but is preferably the same as the solid support to which the microorganisms themselves bound. Thus, in a further aspect, the present invention provides a method of analysing a microorganism containing sample, said method comprising:
  (a) binding said microorganisms to a solid support by means of a non-specific ligand immobilised on said solid support; and
  (b) identifying the microorganisms bound to said solid support.

Step (b) is conveniently performed by
  (c) lysing the microorganisms; and optionally
  (d) binding nucleic acid released from said lysed microorganisms to a solid support.

Alternatively viewed, the invention provides a method of detecting a cell type or microorganism in a sample, said method comprising steps (a) and (b) as described above.

Suitable methods for lysing the microorganisms, binding the nucleic acid thus released and analysing the nucleic acid are provided in WO98/51693 which is incorporated herein by reference. Thus, a further aspect of the present invention is a method of isolating nucleic acid from a sample of cells, said method comprising:
  (a) binding cells in said sample to a solid support by means of a non-specific ligand immobilised on said solid support;
  (b) lysing the bound cells; and
  (c) binding nucleic acid released from said lysed cells to a solid support.

A still further aspect is a method for detecting the presence or absence of a target cell in a sample, said method comprising:
  (a) binding cells in said sample to a solid support by means of a non-specific ligand immobilised on said solid support;

(b) lysing the bound cells;
(c) binding nucleic acid released from said lysed cells to a solid support; and
(d) detecting the presence or absence of nucleic acid characteristic of said target cells within said bound nucleic acid. Preferred cells, ligands and solid supports are as discussed above.

The nucleic acid may be DNA, RNA or any naturally occurring or synthetic modification thereof, and combination thereof. Preferably however the nucleic acid will be DNA, which may be single or double stranded or in any other form, e.g. linear or circular.

Following binding, the isolated or support-bound microorganism, are lysed to release their nucleic acid. Methods of cell lysis are well known in the art and widely described in the literature and any of the known methods may be used. Different methods may be more appropriate for different microorganisms, but any of the following methods could, for example, be used: detergent lysis using eg. SDS, LiDS or sarkosyl in appropriate buffers; the use of chaotropes such as Guanidium Hydrochloride (GHCl), Guanidium thiocyanate (GTC), sodium iodide (NaI), perchlorate etc; mechanical disruption, such as by a French press, sonication, grinding with glass beads, alumina or in liquid nitrogen; enzymatic lysis, for example using lysozyme, proteinases, pronases or cellulases or any of the other lysis enzymes commercially available; lysis of cells by bacteriophage or virus infection; freeze drying; osmotic shock; microwave treatment; temperature treatment; eg. by heating or boiling, or freezing, eg. in dry ice or liquid nitrogen, and thawing; alkaline lysis. As mentioned above, all such methods are standard lysis techniques and are well known in the art, and any such method or combination of methods may be used.

Conveniently, lysis may be achieved according to the present invention by using chaotropes and/or detergents. For example, in the case of bacterial cells, the combination of a chaotrope with a detergent has been found to be particularly effective. An exemplary suitable lysis agent thus includes a chaotrope such as GTC or GHCl and a detergent such as SDS or Sarkosyl. The lysis agents may be supplied in simple aqueous solution, or they may be included in a buffer solution, to form a so-called "lysis buffer". Any suitable buffer may be used, including for example Tris, Bicine, Tricine and phosphate buffers. Alternatively the lysis agents may be added separately. Suitable concentrations and amounts of lysis agents will vary according to the precise system, nature of the calls etc. and may be appropriately determined, but concentrations of eg. 2M to 7M chaotropes such as GTC GHCl, NaI or Verchlorate may be used, 0.1M to 1M alkaline agents such as NaOH, and 0.1 to 50% (w/v) eg. 0.5 to 15% detergent. Thus, an example of a suitable representative lysis buffer includes an aqueous solution of 4M GTC, 1% (w/v) sarkosyl.

The isolated, support-bound microorganisms, may conveniently be removed or separated from the remainder of the sample, thereby concentrating or enriching the cells. Thus the cell binding step serves to enrich the cells or to concentrate them in a smaller volume than the initial sample. Lysis then may conveniently be achieved by adding an appropriate lysis buffer containing the desired lysis agents or by subjecting the isolated cells to the desired lysis conditions. For example, in the case of simply adding a lysis buffer containing appropriate lysis agents, the isolated cells may simply be incubated in the presence of the lysis buffer for a suitable interval to allow lysis to take place. Different incubation conditions may be appropriate for different lysis systems, and are known in the art. For example for a detergent and/or chaotrope containing lysis buffer, incubation may take place at room temperature or at higher temperatures eg. 37° C. or 65° C. Likewise, time of incubation may be varied from a few minutes eg. 5 or 10 minutes to hours, eg. 1 to 2 hours. In the case of GTC/sarkosyl lysis buffers and bacterial cells, incubation at eg. 65° C. for 10-20 minutes has been found to be appropriate, but this may of course be varied according to need. For enzymatic lysis, eg. using proteinase K etc, longer treatment times may be required, eg. overnight.

Following lysis, the released nucleic acid is conveniently bound to a solid support, preferably the one to which the lysed microorganisms are bound. Although, for example, a mixed population of beads may be provided some with a non-specific ligand for binding to microorganisms and others adapted to bind nucleic acid.

This nucleic acid binding may be achieved in any way known in the art for binding nucleic acid to a solid support. Conveniently, the nucleic acid is bound non-specifically to the support ie. independently of sequence. Thus, for example the released nucleic acid may be precipitated onto the support using any of the known precipitants for nucleic acid, eg. alcohols, alcohol/salt combinations, polyethylene glycols (PEGs) etc. Precipitation of nucleic acids onto beads in this manner is described for example in WO 91/12079. Thus, salt may be added to the support and released nucleic acid in solution, followed by addition of alcohol which will cause the nucleic acid to precipitate. Alternatively, the salt and alcohol may be added together, or the salt may be omitted. As described above in relation to the cell binding step, any suitable alcohol or salt may be used, and appropriate amounts or concentrations may readily be determined.

Alternative non-specific nucleic acid-binding techniques include the use of detergents as described in WO 96/18731 of Dynal AS (the so-called "DNA Direct" procedure), and the use of chaotropes and a nucleic acid-binding solid phase such as silica particles as described by Akzo N. V. in EP-A-0389063.

Ionic binding of the nucleic acid to the support may be achieved by using a solid support having a charged surface, for example a support coated with polyamines.

The support which is used in the method of the invention may also carry functional groups which assist in the specific or non-specific binding of nucleic acids, for example DNA binding proteins eg. leucine zippers or histones or intercalating dyes (eg. ethidium bromide or Hoechst 42945) which may be coated onto the support.

Likewise, the support may be provided with binding partners to assist in the selective capture of nucleic acids. For example, complementary DNA or RNA sequences, or DNA binding proteins may be used, or viral proteins binding to viral nucleic acid. The attachment of such proteins to the solid support may be achieved using techniques well known in the art.

A convenient method of precipitating the nucleic acid according to the invention is by adding a precipitant, eg. alcohol, to the mixture containing the support and lysed cells. Thus, an appropriate volume of alcohol, eg. 100% or 96% ethanol, may simply be added to the mixture, and incubated for a time period sufficient to allow the released nucleic acid to become bound to the support. The incubation conditions for this step are not critical and may simply comprise incubating at 5-10 minutes at room temperature. However, the length of time may be varied, and temperature increased according to choice.

Although not necessary, it may be convenient to introduce one or more washing steps to the isolation method of the invention, for example following the nucleic acid binding step. Any conventional washing buffers or other media may be used. Generally speaking, low to moderate ionic strength buffers are preferred eg. 10 mM Tris-HCl at pH 8.0/10 mM NaCl. Other standard washing media, eg. containing alcohols, may also be used, if desired, for example washing with 70% ethanol.

The use of magnetic particles permits easy washing steps simply by aggregating the particles, removing the nucleic acid binding medium, adding the washing medium and reaggregating the particles as many times as required.

Following the nucleic acid isolation process and any optional washing steps which may be desired, the support carrying the bound nucleic acid may be transferred eg. resuspended or immersed into any suitable medium eg. water or low ionic strength buffer. Depending on the support and the nature of any subsequent processing desired, it may or may not be desirable to release the nucleic acid from the support.

In the case of a particulate solid support such as magnetic or non-magnetic beads, this may in many cases be used directly, for example in PCR or other amplifications, without eluting the nucleic acid from the support. Also, for many DNA detection or identification methods elution is not necessary since although the DNA may be randomly in contact with the bead surface and bound at a number of points by hydrogen bonding or ionic or other forces, there will generally be sufficient lengths of DNA available for hybridisation to oligonucleotides and for amplification.

However, if desired, elution of the nucleic acid may readily be achieved using known means, for example by heating, e.g. to 70-90° C. for 5 to 10 minutes, following which the support may be removed from the medium leaving the nucleic acid in solution. Such heating is automatically obtained in PCR by the DNA denaturation step preceding the cycling program.

If it is desired to remove RNA from DNA, this may be achieved by destroying the RNA before the DNA separation step, for example by addition of an RNAase or an alkali such as NaOH.

An advantage of the present invention, is that it is quick and simple to perform, and the simplicity of the method allows for high throughput of samples.

The invention is advantageously amenable to automation, particularly if particles, and especially, magnetic particles are used as the support.

As mentioned above, the method of the invention has particular utility as a preliminary first step to prepare nucleic acid for use in nucleic acid-based detection procedures.

As mentioned above, advantageously bound nucleic acid need not be eluted or removed from the support prior to carrying out the detection step, although this may be performed if desired. Whether or not the nucleic acid is eluted may also depend on the particular method which was used in the nucleic acid binding step. Thus certain nucleic acid-binding procedures will bind the nucleic acid more tightly than others. In the case of DNA-binding using detergents (eg. by DNA Direct) for example, the nucleic acid will elute from the solid support when an elution buffer or other appropriate medium is introduced. Nucleic acid bound by means of a precipitant such as alcohol or a chaotrope will remain more tightly bound and may not elute when placed in a buffer medium, and may require heating to be eluted.

Thus, the support-bound nucleic acid may be used directly in a nucleic acid based detection procedure, especially if the support is particulate, simply by resuspending the support in, or adding to the support, a medium appropriate for the detection step. Either the nucleic acid may elute into the medium, or as mentioned above, it is not necessary for it to elute. When sulphated sugars are used as a ligand, elution is preferred.

A number of different techniques for detecting nucleic acids are known and described in the literature and any of these may be used according to the present invention. At its simplest the nucleic acid may be detected by hybridisation to a probe and very many such hybridisation protocols have been described (see eg. Sambrook et al., 1989, Molecular Cloning: A Laboratory Manual, 2nd Ed. Cold Spring Harbor Press, Cold Spring Harbor, N.Y.). Most commonly, the detection will involve an in situ hybridisation step, and/or an in vitro amplification step using any of the methods described in the literature for this. Thus, as mentioned, techniques such as LAR, 3SR and the Q-beta-replicase system may be used. However, PCR and its various modifications eg. the use of nested primers, will generally be the method of choice (see eg. Abramson and Myers, 1993, Current Opinion in Biotechnology, 4:41-47 for a review of nucleic acid amplification technologies).

Other detection methods may be based on a sequencing approach, for example, the minisequencing approach as described by Syvänen and Söderlund, 1990, Genomics, 8: 684-692.

In amplification techniques such as PCR, the heating required in the first step to melt the DNA duplex may release the bound DNA from the support. Thus, in the case of a subsequent detection step, such as PCR, the support bound nucleic acid may be added directly to the reaction mix, and the nucleic acid will elute in the first step of the detection process. The entire isolated support bound nucleic acid sample obtained according to the invention may be used in the detection step, or an aliquot.

The results of the PCR or other detection step may be detected or visualised by many means, which are described in the art. For example the PCR or other amplification products may be run on an electrophoresis gel eg. an ethidium bromide stained agarose gel using known techniques. Alternatively, the DIANA system may be used, which is a modification of the nested primer technique. In the DIANA (Detection of Immobilised Amplified Nucleic Acids) system (see Wahlberg et al., Mol. Cell Probes 4:285(1990)), the inner, second pair of primers carry, respectively, means for immobilisation to permit capture of amplified DNA, and a label or means for attachment of a label to permit recognition. This provides the dual advantages of a reduced background signal, and a rapid and easy means for detection of the amplified DNA. Real-time PCR methods may be used in DNA detection, e.g. 5'nuclease PCR or techniques using fluorescent probes.

The amplified nucleic acid may also be detected, or the result confirmed, by sequencing, using any of the many different sequencing technologies which are now available, eg. standard sequencing, solid phase sequencing, cyclic sequencing, automatic sequencing and minisequencing.

The various reactants and components required to perform the methods of the invention may conveniently be supplied in kit form. Such kits represent a further aspect of the invention.

At its simplest, this aspect of the invention provides a kit for isolating microorganisms from a sample comprising:
  (a) a solid support having immobilised thereon a ligand which is capable of non-specific binding to microorganisms;
  (b) means for binding microorganisms to said solid support; optionally (c) means for lysing said cells; and optionally
(d) means for binding nucleic acid released from said lysed cells to a solid support.

The various means (b), (c) and (d) may be as described and discussed above, in relation to the method of the invention.

A typical kit may comprise a solid support, e.g. particles coated with a polysaccharide such as GUM1, a binding buffer, e.g. PBS and a lysis buffer.

A further optional component is (e), means for detecting the presence or absence of nucleic acid characteristic of a target microorganism. As discussed above, such means may include appropriate probe or primer oligonucleotide sequences for use in hybridisation and/or amplification-based detection techniques.

Optionally further included in such a kit may be buffers, salts, polymers, enzymes etc.

The kits of the invention are of great practical utility in the extraction of bacteria and isolation of DNA for PCR amplification. A suitable protocol for use with the kit would be as follows, it is assumed that magnetic or magnetisable beads have been chosen as the solid support (a):
  combine binding buffer (b) and beads, add a sample from an overnight culture and mix, e.g. in an Eppendorf tube,
  place under the influence of a magnet and allow the bacteria/bead complex to move to the side of the tube,
  pipette off and discard the supernatant,
  add the lysis buffer (c) and incubate with ethanol,
  use the magnet to separate the beads from the supernatant and pipette off and discard the supernatant,
  wash the beads and remove supernatant,
  resuspend the bead/DNA sample for PCR.

According to a further aspect of the present invention is provided the use of a solid support as described herein in the gross separation of cells from a sample. The separation is 'gross' because it is not a cell-specific isolation method, rather a general method of isolating cells (e.g. microorganisms) present in a sample from the other components. Previously such methods had been achieved by filtration or precipitation. By contrast, the solid supports described herein can be used to combine the advantages of ligand-receptor binding but not in a species or cell-type specific manner. As described herein, the ligands attached to the solid supports are capable of binding to a significant proportion, if not most, of the types of microorganisms (e.g. different bacterial species) or eukaryotic cell types in the sample in order to achieve gross separation thereof from the total sample.

The invention will now be described in more detail in the following non-limiting Examples with reference to the drawings in which.

EXAMPLE 1

Figure 1:
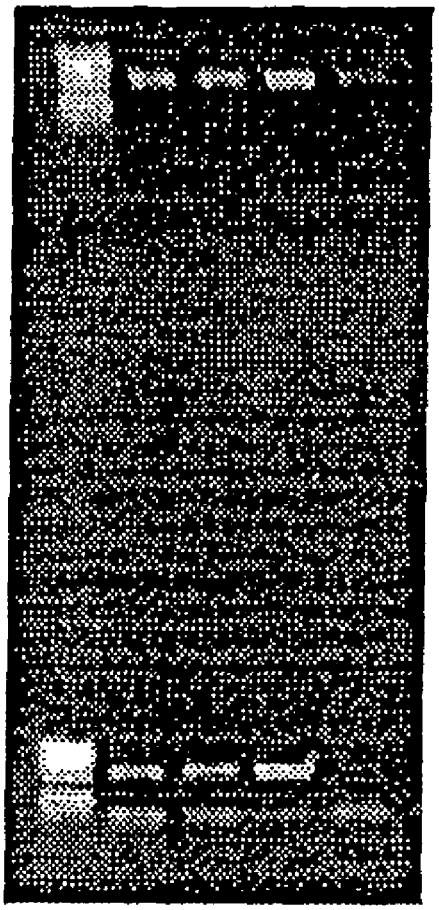
FIG. 1 is a photograph of a gel showing PCR products from the nucleic acid of bacteria (*E. coli*) bound to beads coated with mannose, maltose and GUM1.

Manufacturing of Carbohydrate Coated Particles and Testing of Cell Binding Properties The Compound were Coupled on M-PVA OCN-activated Beads (Chemagen AG). Reaction:

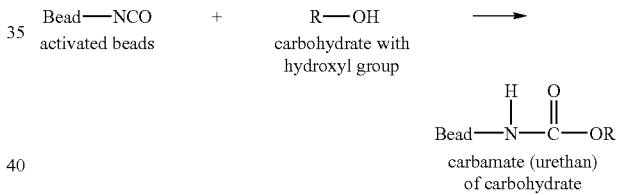

The modified beads were incubated with different bacterial cultures, either with pure undiluted cultures (o.n.) or cultures diluted in water or in a buffer (PBS). In order to investigate cell binding, DNA was isolated from the bacteria-bead complex, and subsequently analysed by performing PCR. Ref: WO 98/51693. This coupling reaction was performed by Chemagen and the resulting modified beads used in the isolation methods of the invention discussed herein.

EXAMPLE 2

Protocol for Isolation of Bacteria on Beads and Identification of Specific Bacteria The bacteria were grown overnight in 100 ml Tryptone Soya Broth at 30° C. with no agitation. 800 µl PBS (binding buffer) and 10 µl beads according to the invention (10 mg/ml) were mixed, then 100 µl of the overnight culture were added and gently mixed by pipetting. The tube was left at room temperature for 5 min. The supernatant was removed by using a magnetic separator and the bead-bacteria complex was resuspended in 50 µl lysis buffer (4M guaridine thiocyanate-1% sarkosyl). The samples were incubated at 65° C. for 5 minutes with lids open.

Then 100 μl 96% ethanol were added, and the incubation was continued for 5 minutes with lids closed. The supernatant was removed using the magnetic separator and the bead-DNA sample was washed twice with 1 ml 70% ethanol.

The bead-DNA sample was resuspended in 45 μl H$_2$O and incubated at 65° C. for 15 minutes with lids open to remove all traces of ethanol (as an alternative, 5 μl H$_2$O may be added to moisten the beads which are then incubated at 65° C. for 5 mins). 20 μl of the purified material was used in one 50 μl PCR.

To identify the bacteria isolated, PCR amplification with species- or group-specific primers (X and Y) was performed.

Table 1 below gives suitable primers for different bacteria.

TABLE 1

| Genus | | Primer sequence | Product size (bp) |
|---|---|---|---|
| Salmonella<br>Escherichia<br>Shigella | UPPER:<br>LOWER: | 5' AAG TCG AAC GGT AAC AGG A 3'<br>5' CAC CGC TAC ACC TG(G/A)AAT 3' | 614 |
| Escherichia,<br>pathogenic | UPPER:<br>LOWER: | 5' ACT GAG ATT AAG GCT GAT AA 3'<br>5' ACA TTA ACC CCA GGA AGA G 3' | 782 |
| Yersinia<br>Aeromonas<br>Vibrio | UPPER:<br>LOWER: | 5' CAC ATG CAA GTC GAG GGG G 3'<br>5' CAC CGC TAC ACC TG(GA) AAT 3' | 620 |
| Listeria<br>Bacillus | UPPER:<br>LOWER: | 5' G(AT)T CCT GAA ACC GTG TGC C 3'<br>5' CCT TCC GGT CTG ACT TCA 3' | 702 |
| Campylobacter | UPPER1:<br>UPPER2:<br>LOWER: | 5' AAT CAC AGC AGT CAG GCG 3'<br>5' CGT AAT AGC TCA CTG GTC T 3'<br>5' GTC GGT TTA CGG TAC GGG 3' | 921<br>761 |
| Clostridium | UPPER:<br>LOWER: | 5' CGA AGG CGG CTT TCT GGA 3'<br>5' GCG ATT ACT AGC AAC TCC 3' | 609 |
| Citrobacter<br>Hafnia<br>Kiebsiella<br>Enterobacter | UPPER:<br>LOWER: | 5' AAG TCG AAC GGT AGC ACA G 3'<br>5' CAC CGC TAC ACC TG(G/A)AAT 3' | 634 |
| Proteus<br>Morganella<br>Photobacterium<br>Serratia<br>Shewanella | UPPER:<br>LOWER: | 5' CTA ACA CAT GCA AGT CGA G 3'<br>5' CAC CGC TAC ACC TG(G/A)AAT 3' | 625 |
| Streptococcus<br>Lactococcus<br>Staphylococcus<br>Enterococcus<br>Leuconostoc<br>Pediococcus<br>Lactobacillus<br>Brochothrix | UPPER:<br>LOWER: | 5' TGC CTT TTG TAG AAT GAC G 3'<br>5' CGC CAT TCT CAC TTC TAA GC 3' | 680 |

PCR amplification was carried out in 50 μl volume: H$_2$O-17.5 μl; dNTP 2 mM-5 μl; 10× buffer DynaZyme-5 μl; primer x (10 pmol/μl)-1 μl; primer y 10 pmol/μl-1 μl; enzyme DynaZyme 2 U/μl-0.5 μl; template-20 μl. The temperature program was: 94° C.-4 min, then 35 cycles with the parameters 96° C.-15 seco; 56° C.-30 sec; 72° C.-1 min; followed by 72° C.-7 min.

The PCR products were visualized by agarose gel electrophoresis.

EXAMPLE 3

The protocol of Example 2 was performed with M-PVA beads with D-mannose coupled thereto.

The beads were shown to bind to Bacillus, *E. coli* (pathogen and non-pathogen), *Listeria, Salmonella, Yersinia*.

EXAMPLE 4

The protocol of Example 2 was performed with M-PVA beads with maltose coupled thereto.

The beads were shown to bind to Bacillus, *E. coli* (pathogen and non-pathogen), *Listeria, Salmonella, Yersinia*.

EXAMPLE 5

The protocol of Example 2 was performed with M-PVA beads with galactomannan polysaccharide (GUM1) coupled thereto.

The beads were shown to bind to inter alia *Aeromonas, Bacillus, Campylobacter, Citrobacter, Clostridium, Enterobacter, E. coli* (pathogen and non-pathogen), *Hafnia, Klebsiella, Listeria, Proteus, Salmonella, Shewanella, Serratia, Shigella, Vibrio, Yersinia*.

Figure 3:
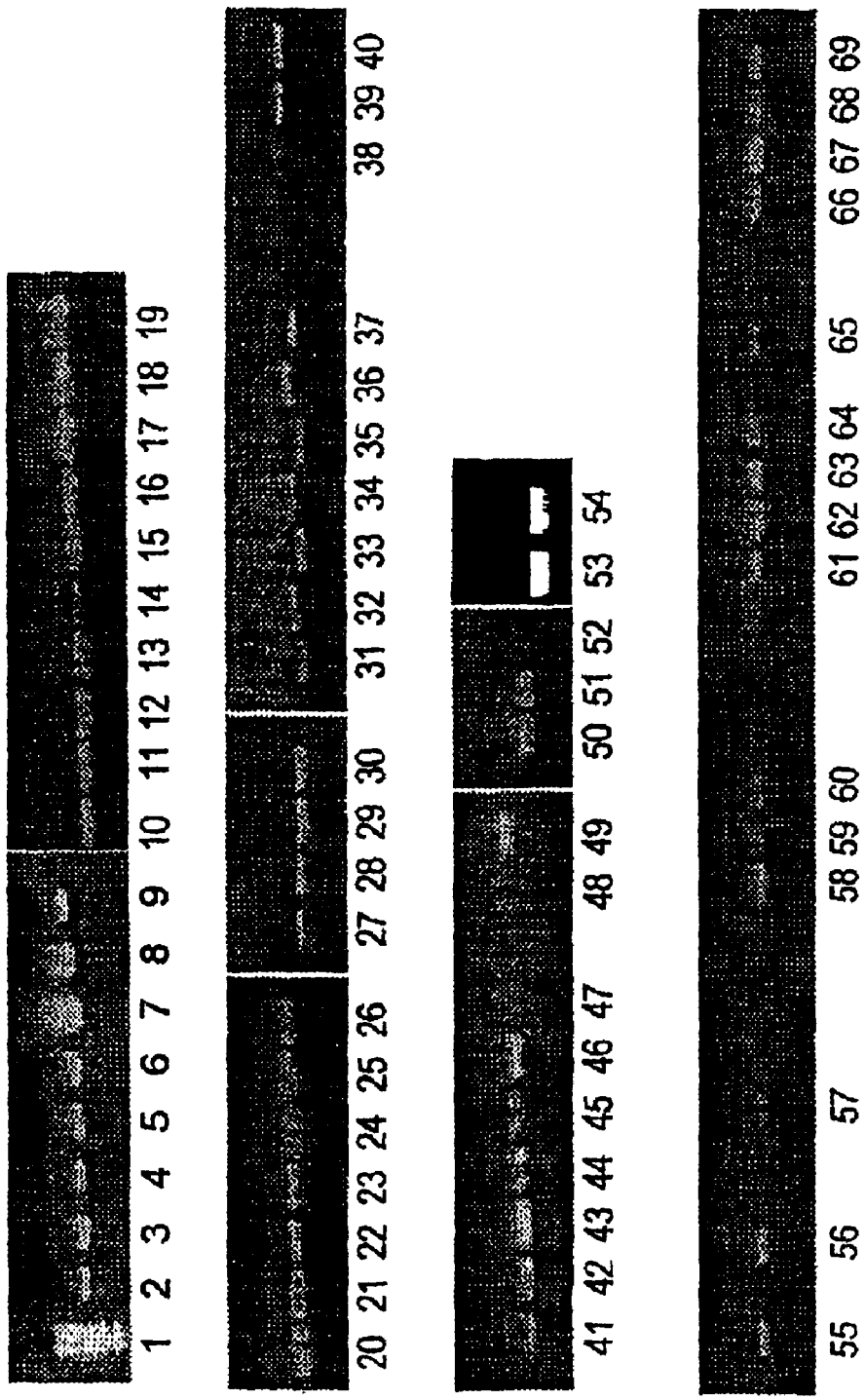
FIG. 3 shows a series of gel photographs indicating binding of a wide variety of bacteria to GUM1 coated beads.

The results of these experiments can be seen in the gel photographs of FIG. 3. Bands of PCR product indicating binding of specific bacteria to the beads according to the following scheme are shown.

Lane 1, DNA marker (GeneRuler™ 100 bp DNA Ladder, Fermentas);

Lanes 2-3, *Klebsiella pneumoniae* and *K. oxytoca*, respectively;

Lanes 4-6, *Shigella flexneri, S. sonnei*, and *S. boydii*, respectively;

Lanes 7-8 and 12-13, *Vibrio cholerae* (lanes 7 and 12), *V. vulnificus* (lane 8), and *V. parahaemolyticus;*
Lane 9, *Hafnia alvei;*
Lanes 10-11, *Aeromonas sobria* and *A. hydrophila,* respectively;
Lanes 12-13, Vibrio, see above;
Lane 14, *Proteus vulgaris;*
Lanes 15-16, *Salmonella enterica ssp typhimurium* and *S. enterica ssp enteritidis,* respectively;
Lanes 17-18, and 41-44, *Yersinia enterocolitica* (lanes 17-18 (serotype unknown), serotypes 0:9 (lane 42), 0:8 (lane 43), and 0:3 (lane 44)), and *Y. pseudotuberculosis* (lane 41);
Lane 19, *Escherichia coli;*
Lanes 20-21, *Listeria innocua* and *L. monocytogenes,* respectively;
Lanes 22-23 and 38-39, *Bacillus cereus* (lane 22), *B. subtilis* (lane 23), and *B. simplex* (lanes 38-39);
Lane 24, *Citrobacter freundii;*
Lanes 25-26, *Clostridium perfringens* and *C. sordelli,* respectively;
Lanes 27-30, *Escherichia coil,* pathogenic
Lane 31-37, *Campylobacter jejuni* (lane 31) and *C. lari* (lanes 32-37);
Lanes 38-39, Bacillus, see above;
Lane 40, *Brochothrix thermosphacta;*
Lanes 41-44, Yersinia, see above;
Lanes 45-47, *Enterobacter sakazakii, E. aerogenes,* and *E. cloacae,* respectively;
Lane 48, *Morganella morganii;*
Lane 49, *Serratia marcescens;*
Lanes 50-52, *Shewanella putrefaciens;*
Lanes 53-54, *Photobacterium phosphoreum* and *P. damsela,* respectively;
Lane 55, *Streptococcus thermophilus;*
Lane 56, *Lactococcus lactis;*
Lane 57, *Staphylococcus warneri;*
Lane 58, *Enterococcus faecalis;*
Lanes 59-60, *Leuconostoc mesenteroides;*
Lanes 61-64, *Pediococcus acidilactici* (lanes 61-62) and *P. damnosus* (lanes 63-64);
Lanes 65-69, *Lactobacillus acidophilus* (lanes 65, 68 and 69) and *L. plantarum* (lanes 66-67).

EXAMPLE 6

*E. coli* was isolated from an overnight culture using the beads of Examples 3, 4 and 5 and Dynabeads M-280 (Dynal, Norway) (unactivated). After lysis to release nucleic acid, an *E. coli* DNA sequence of approximately 600 bp was amplified using the primers U59/L673 (see Table 1).

The results are shown in FIG. 1 in which
Lanes 2-5, 15 µl template was used and in lanes 7-10, 5 µl template was used;
Lane 1 and 6, DNA marker φx174/HaeIII;
Lane 2 and 7, mannose-coated beads;
Lane 3 and 8, maltose-coated beads;
Lane 4 and 9, GUM1 coated beads;
Lane 5 and 10, Dynabeads M-280 activated.

EXAMPLE 7

*B. cereus* ATCC 14579 was isolated using the beads of Example 5 and uncoated beads given the reference UNC from 2 ml of overnight culture (100 ml TSB at 30° C.) according to the following dilutions:
Lane 1, DNA marker φx174/HaeIII;
Lane 2, 100 µg UNC, undiluted culture;
Lane 3, 50 µg GUM1, $10^1$ diluted culture;
Lane 4, 100 µg GUM1, $10^1$ diluted culture;
Lane 5, 200 µg GUM1, $10^1$ diluted culture;
Lane 6, 100 µg UNC, $10^1$ diluted culture;
Lane 7, 50 µg GUM1, $10^2$ diluted culture;
Lane 8, 100 µg GUM1, $10^2$ diluted culture;
Lane 9, 200 µg GUM1, $10^2$ diluted culture;
Lane 10, 100 µg UNC, $10^2$ diluted culture;
Lane 11, 50 µg GUM1, $10^3$ diluted culture;
Lane 12, 100 µg GUM1, $10^3$ diluted culture;
Lane 13, DNA marker φx174/HaeIII;
Lane 14, 200 µg GUM1, $10^3$ diluted culture;
Lane 15, 100 µg UNC, $10^3$ diluted culture;
Lane 16, 50 µg GUM1, $10^4$ diluted culture;
Lane 17, 100 µg GUM1, $10^4$ diluted culture;
Lane 18, 200 µg GUM1, $10^4$ diluted culture;
Lane 19, 100 µUNC, $10^4$ diluted culture;
Lane 20, 50 µg GUM1, $10^5$ diluted culture;
Lane 21, 100 µg GUM1, $10^5$ diluted culture;
Lane 22, 200 µg GUM1, $10^5$ diluted culture;
Lane 23, 100 µg UNC, $10^5$ diluted culture.

Figure 2:
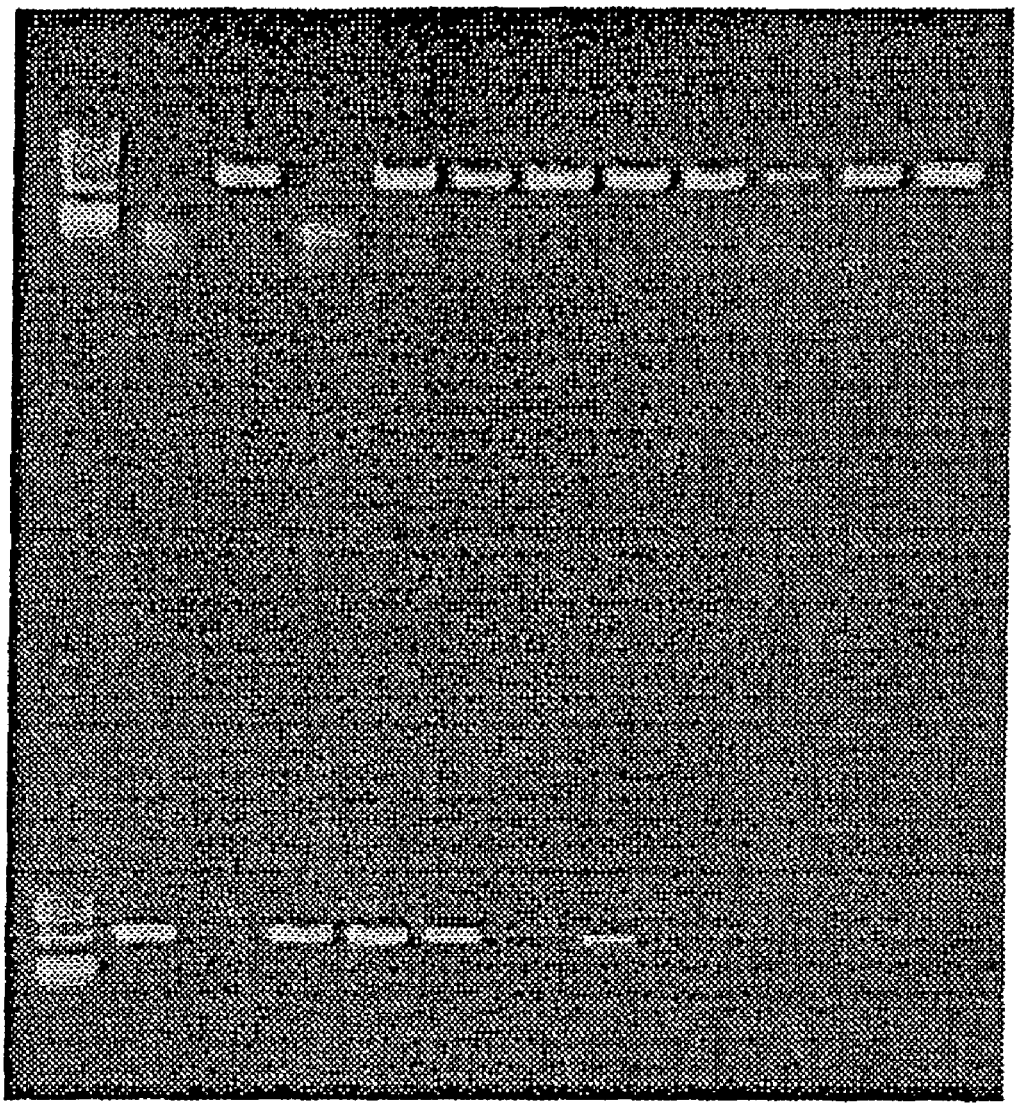
FIG. 2 is a photograph of a gel showing PCR products from the nucleic acid of bacteria (*B. cereus*) bound to GUM1 coated beads and uncoated beads.

After lysis to release nucleic acid, a *B. cereus* sequence of approximately 600 bp was amplified using the primers U552/L1254 (see Table 1). The results are shown in FIG. 2. The result for a 10' dilution would appear to be an error since 50 µg of GUM1 and 200 µg GUM1 both gave positive results for the detection of nucleic acid, indicative of cell binding. Overall, the results show that binding is 100-1000 times better for GUM1 than for the uncoated beads.

EXAMPLE 8

Other beads have been used to illustrate the principles of the invention, a particularly suitable bead type are Dynabeads M-270 Epoxy, Prod. No. 143.02 (available from Dynal AS, Norway)

Preparation of Beads 2 ml of sterile filtrated 0.1 M sodium phosphate buffer, pH 7.4, was added to 30 mg dry beads to give a concentration of approximately $10^9$ beads per ml. The beads were resuspended by vortexing for 30 seconds, and then incubated with slow tilt rotation for ten minutes. The tube was placed on a magnet for 4 minutes and the supernatant was carefully pipetted off.

2 ml of 0.1 M sodium phosphate buffer, pH 7.4, was added to the tube again and the beads were mixed properly by vortexing. The tube was placed on a magnet for 4 minutes and the supernatant was removed.

The washed beads were resuspended in 600 µl 0.1 M sodium phosphate buffer, pH 7.4, to give the recommended bead concentration and ammonium sulfate concentration after addition of ligand solution. This bead solution was used in the coating procedure.

Coating Procedure

The ligand was dissolved in PBS to a concentration of 1 mg/ml and sterile filtrated.

600 µl of the ligand was mixed with 600 µl bead solution and 600 µl sterile filtrated 3M ammonium sulphate according to Dynal's recommendation. The tube was incubated with slow rotation overnight at room temperature.

After the incubation the tube was placed on a magnet for 4 minutes and the supernatant was removed. The coated beads were washed a total of four times with 2 ml PBS. The beads were finally resuspended in 1 ml PBS to a concentration of 30 mg/ml and stored at 4° C.

EXAMPLE 9

Protocol for Isolation of Bacteria on Beads and Identification of Specific Bacteria The bacteria were grown overnight in 100 ml Tryptone Soya Broth at 37° C. 800 µl PBS (binding buffer) and 20 µl beads according to the invention (10 mg/ml) were mixed, then 100 µl of the overnight culture were added and gently mixed by pipetting. The tube was left at room temperature for 5 min. The supernatant was removed by using a magnetic separator and the bead-bacteria complex was resuspended in 50 µl lysis buffer (4M guanidine thiocyanate-1% sarcosyl). The samples were incubated at 80° C. for 5 minutes with lids closed.

Then 150 µl 96% ethanol was added, and the incubation was continued for 5 minutes. The supernatant was removed using the magnetic separator, and the bead-DNA sample was washed twice with 1 ml 70% ethanol.

The bead-DNA sample was resuspended in 30 µl $H_2O$ and incubated at 80 for 10 minutes with lids open to remove all traces of ethanol. All 30 µl of the purified material was used in one 50 µl PCR.

EXAMPLE 10

Bacteria were isolated using the protocol of Example 9 and to identify the bacteria isolated, PCR amplification with the following primers was performed:
Experiments A-E
As in Table 1
Experiment F
UPPER: 5' TGCTTTACACATGCAAGTCG 3'
LOWER: 5' CAT CTC TAC GCA TTT CAT TG 3'

The beads used in the following experiments are M-270 Dynabeads from Dynal AS or M-PVA OCN-activated beads from Chemagen AG.

The bacteria used in the following Experiments A-G are as follows:

| | |
|---|---|
| Aeromonas hydrophila | CCUG 25942 |
| Bacillus cereus | ATCC 11778 |
| Bacillus cereus | NVH 0075-95 |
| Campylobacter jejuni | CCUG 25903 |
| Clostridium perfringens | ATCC 13124 |
| Escherichia coli | ATCC 25922 |
| Escherichia coli | CCUG 38081 |
| Helicobacter pylori | CCUG 38771 |
| Listeria monocytogenes | ATCC 35152 |
| Listeria monocytogenes | CCUG 15527 |
| Neisseria gonorrhoeae | ATCC 49226 |
| Salmonella typhimurium | ATCC 14028 |
| Salmonella typhimurium | CCUG 31969 |
| Shigella flexneri | CCUG 38947 |
| Streptococcus pyogenes | CCUG 30917 |
| Streptococcus pneumoniae | CCUG 33062 |
| Vibrio cholerae | CCUG 42534 |
| Yersinia enterocolitica | Noma ref 102, Y842 |

In the following experiments, amplification was generally performed directly on the DNA-bead complex. However, identification of bacterial species using amplification techniques may be performed on the supernatant. For certain binding ligands such as heparin, dextran sulphate and carrageenan, this may be preferred as the sulphate group may inhibit the PCR reaction. In the following experiments, unless otherwise indicated, when a carrageenan coating is used, the PCR is performed on the supernatant following incubation of the beads at 80° C. to release all the DNA from the beads.

In this Example "carrageenan" refers to iota carrageenan (Sigma, C-3889). Heparin and dextran sulphate were obtained from Sigma, catalogue reference numbers H3149 and D6924 respectively.

Figure 4:
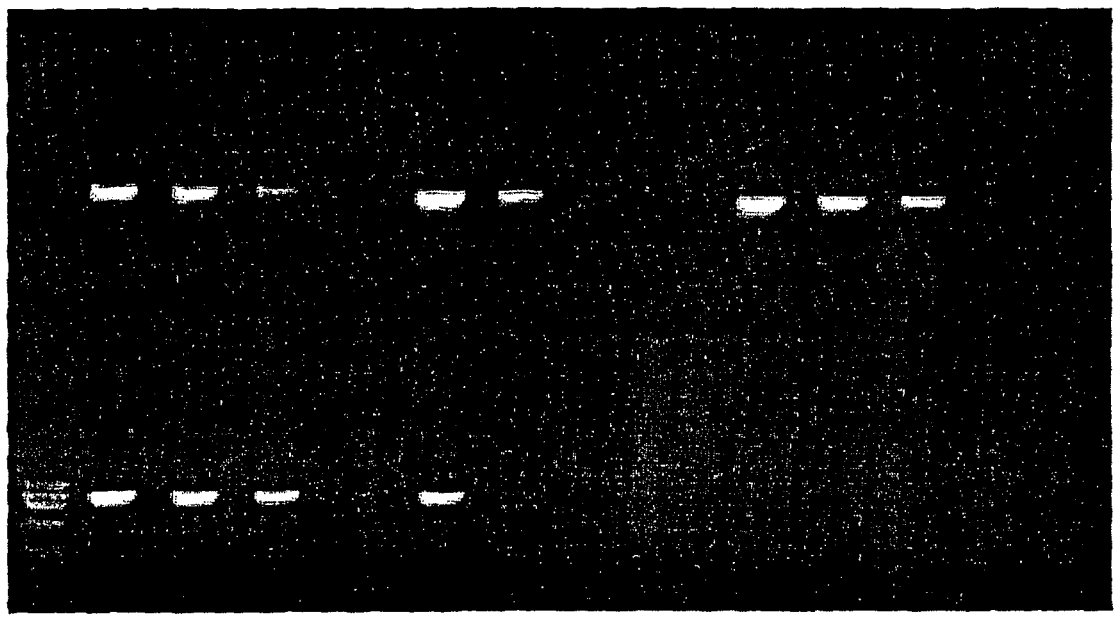
FIG. 4 is a photograph of a gel showing PCR products from the nucleic acid of *Vibrio cholerae* bound to various coated beads.

A. Isolation of Genomic DNA from *Vibrio cholerae* using Gum, Mannose & Carrageenan The results of amplification are shown in the gel photograph of FIG. 4.

Figure 5:
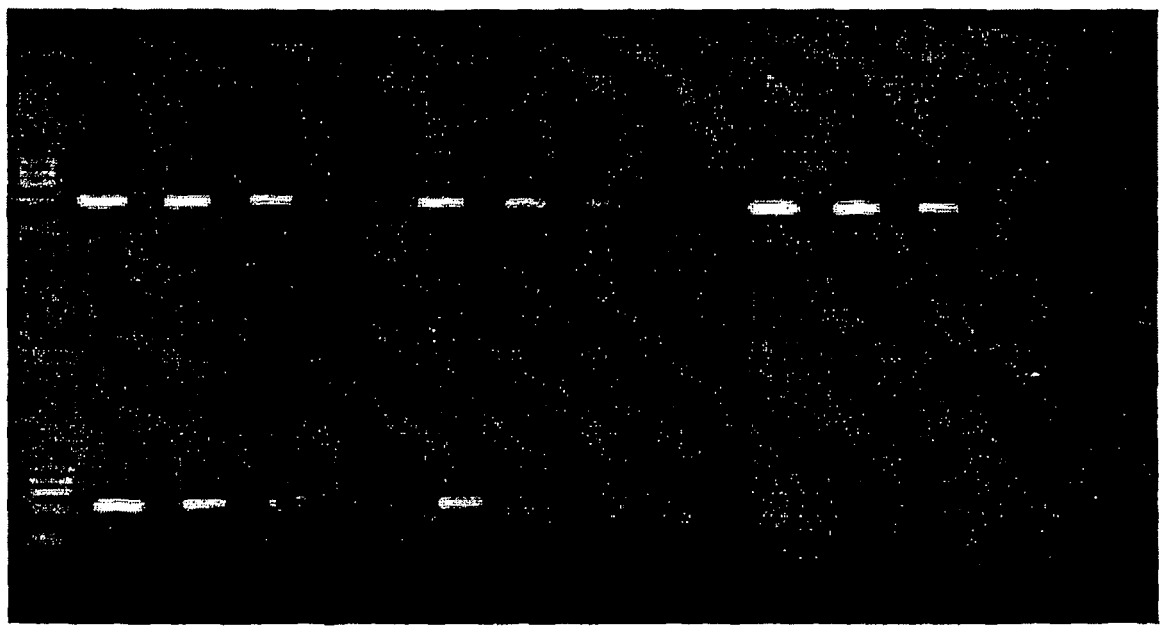
FIG. 5 is a photograph of a gel showing PCR products from the nucleic acid of *Shigella flexneri* bound to various coated beads.

Reading from the top left side on the gel:
Line 1:
Well no 1=Hae III marker (weak)
Well no 2=100 µl $10^{-2}$ dilution of *V. cholerae* added to 200 Mg Dynabeads coated with Gum
Well no 3=100 µl $10^{-3}$ dilution of *V. cholerae* added to 200 µg Dynabeads coated with Gum
Well no 4=100 µl $10^{-4}$ dilution of *V. cholerae* added to 200 µg Dynabeads coated with Gum
Well no 5=100 µl $10^{-1}$ dilution of *V. cholerae* added to 200 µg Dynabeads coated with Gum
Well no 6=100 µl $10^{-2}$ dilution of *V. cholerae* added to 200 µg Dynabeads coated with Mannose
Well no 7=100 µl $10^{-3}$ dilution of *V. cholerae* added to 200 µg Dynabeads coated with Mannose
Well no 8=100 µl $10^{-4}$ dilution of *V. cholerae* added to 200 µg Dynabeads coated with Mannose
Well no 9=100 µl $10^{-5}$ dilution of *V. cholerae* added to 200 µg Dynabeads coated with Mannose
Well no 10=100 µl $10^{-2}$ dilution of *V. cholerae* added to 200 µg Chemagen coated with Carrageenan
Well no 11=100 µl $10^{-3}$ dilution of *V. cholerae* added to 200 µg Chemagen coated with Carrageenan
Well no 12=100 µl $10^{-4}$ dilution of *V. cholerae* added to 200 µg Chemagen coated with Carrageenan
Well no 13=100 µl $10^{-5}$ dilution of *V. cholerae* added to 200 µg Chemagen coated with Carrageenan
Line 2:
Well no 1=Hae III marker
Well no 2=100 µl $10^{-2}$ dilution of *V. cholerae* added to 200 µg Chemagen coated with Gum
Well no 3=100 µl $10^{-3}$ dilution of *V. cholerae* added to 200 µg Chemagen coated with Gum
Well no 4=100 µl $10^{-4}$ dilution of *V. cholerae* added to 200 µg Chemagen coated with Gum
Well no 5=100 µl $10^{-5}$ dilution of *V. cholerae* added to 200 µg Chemagen coated with Gum
Well no 6=100 µl $10^{-2}$ dilution of *V. cholerae* added to 200 µg Chemagen coated with Mannose
Well no 7=100 µl $10^{-3}$ dilution of *V. cholerae* added to 200 µg Chemagen coated with Mannose
Well no 8=100 µl $10^{-4}$ dilution of *V. cholerae* added to 200 µg Chemagen coated with Mannose
Well no 9=100 µl $10^{-5}$ dilution of *V. cholerae* added to 200 µg Chemagen coated with Mannose
Well no 10=negative control B. Isolation of Genomic DNA from *Shigella flexneri*, Using Gum, Mannose, Carrageenan The results of amplification are shown in the gel photograph of FIG. 5.

Figure 6:
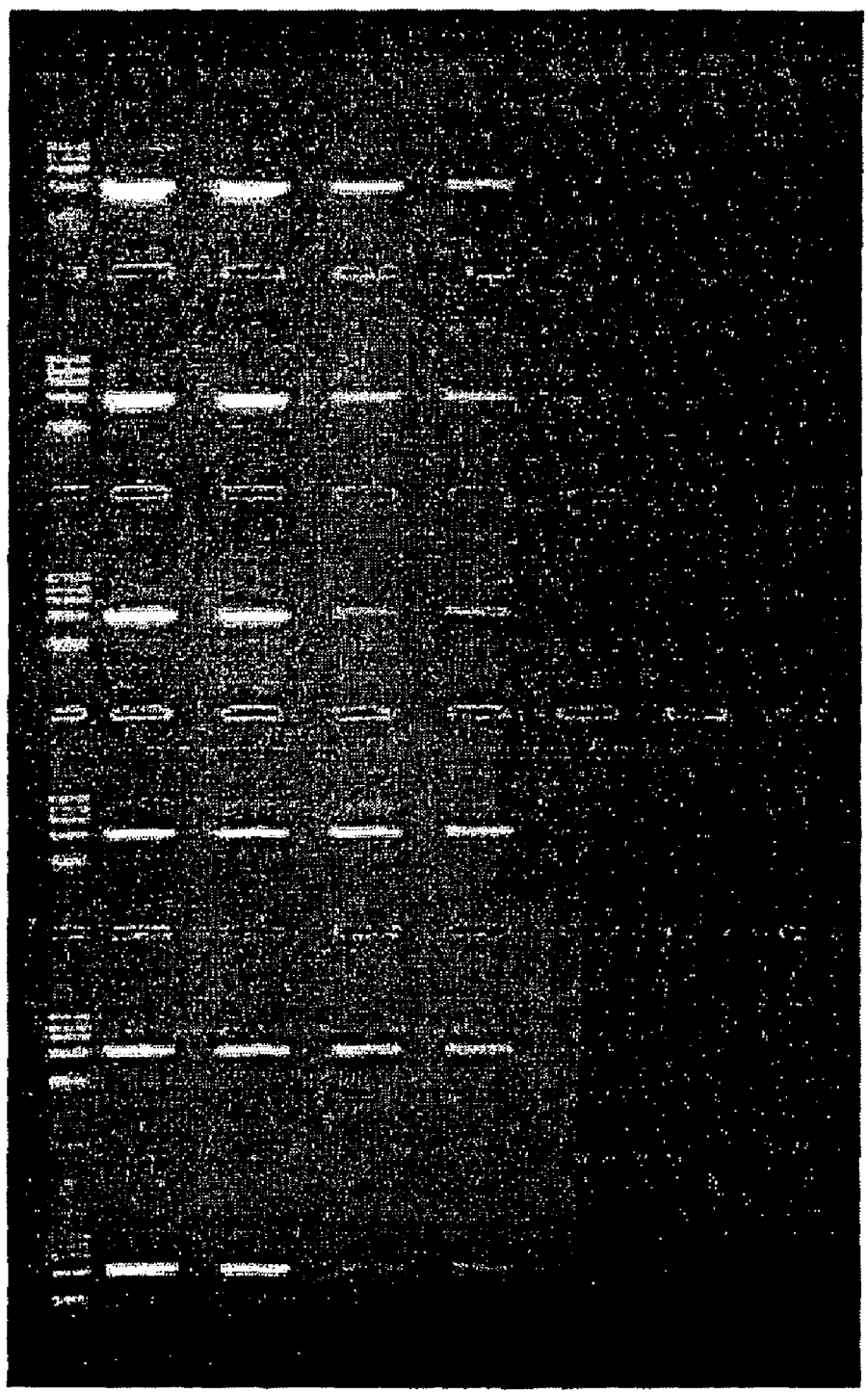
FIG. 6 is a photograph of a gel showing PCR products from the nucleic acid of *E. coli* bound to various coated beads.

Reading from the top left side on the gel:
Line 1:
Well no 1=Hae III marker
Well no 2=100 µl $10^{-2}$ dilution of *S. flexnerii* added to 200 µg Dynabeads coated with Gum
Well no 3=100 µl $10^{-3}$ dilution of *S. flexnerii* added to 200 µg Dynabeads coated with Gum
Well no 4=100 µl $10^{-4}$ dilution of *S. flexnerii* added to 200 µg Dynabeads coated with Gum Well no 5=100 µl $10^{-5}$ dilution of *S. flexnerii* added to 200 µg Dynabeads coated with Gum
Well no 6=100 µl $10^{-2}$ dilution of *S. flexnerii* added to 200 µg Dynabeads coated with Mannose
Well no 7=100 µl $10^{-3}$ dilution of *S. flexnerii* added to 200 µg Dynabeads coated with Mannose
Well no 8=100 µl $10^{-4}$ dilution of *S. flexnerii* added to 200 µg Dynabeads coated with Mannose
Well no 9=100 µl $10^{-5}$ dilution of *S. flexnerii* added to 200 µg Dynabeads coated with Mannose
Well no 10=100 µl $10^{-2}$ dilution of *S. flexnerii* added to 200 µg Chemagen coated with Carrageenan
Well no 11=100 µl $10^{-3}$ dilution of *S. flexnerii* added to 200 µg Chemagen coated with Carrageenan
Well no 12=100 µl $10^{-4}$ dilution of *S. flexnerii* added to 200 µg Chemagen coated with Carrageenan
Well no 13=100 µl $10^{-5}$ dilution of *S. flexnerii* added to 200 µg Chemagen coated with Carrageenan
Line 2:
Well no 1=Hae III marker
Well no 2=100 µl $10^{-2}$ dilution of *S. flexnerii* added to 200 µg Chemagen coated with Gum
Well no 3=100 µl $10^{-3}$ dilution of *S. flexnerii* added to 200 µg Chemagen coated with Gum
Well no 4=100 µl $10^{-4}$ dilution of *S. flexnerii* added to 200 µg Chemagen coated with Gum
Well no 5=100 µl $10^{-5}$ dilution of *S. flexnerii* added to 200 µg Chemagen coated with Gum
Well no 6=100 µl $10^{-2}$ dilution of *S. flexnerii* added to 200 µg Chemagen coated with Mannose
Well no 7=100 µl $10^{-3}$ dilution of *S. flexnerii* added to 200 µg Chemagen coated with Mannose
Well no 8=100 µl $10^{-4}$ dilution of *S. flexnerii* added to 200 µg Chemagen coated with Mannose
Well no 9=100 µl $10^{-5}$ dilution of *S. flexnerii* added to 200 µg Chemagen coated with Mannose C. Isolation of Genomic DNA from *E. coli* Using Carrageenan, Mannose, Gum, Mannan The results of amplification are shown in the gel photograph of FIG. 6.

Figure 7:
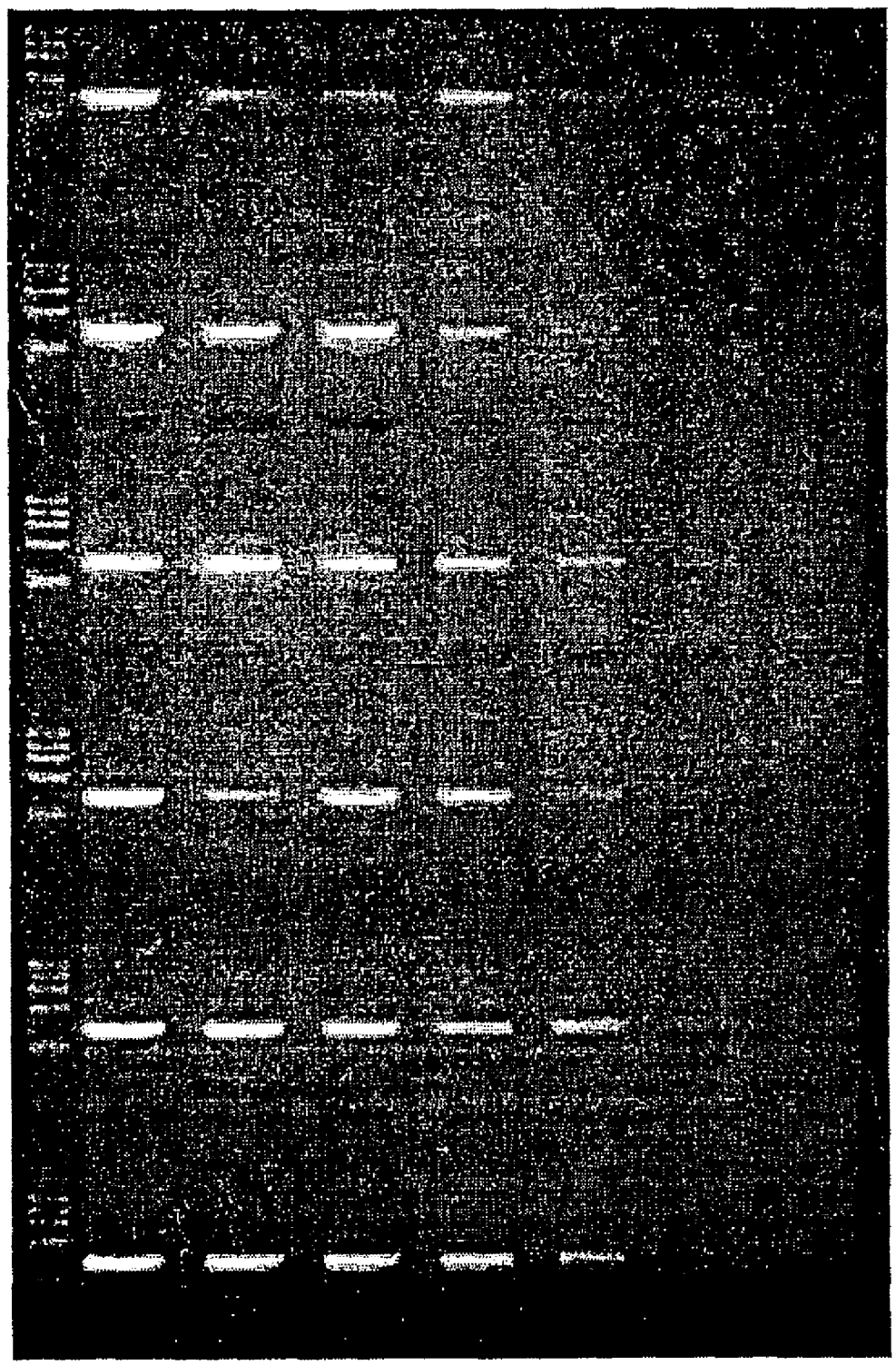
FIG. 7 is a photograph of a gel showing PCR products from the nucleic acid of *Salmonella typhimurium* bound to various coated beads.

There are six lines on the gel all representing *E. coli*
Reading from the top left side on the gel:
Line 1:
Well no 1=Hae III marker
Well no 2=100 µl $10^{-1}$ dilution of *E. coli* added to 200 µg Chemagen beads coated with Carrageenan
Well no 3=100 µl $10^{-2}$ dilution of *E. coli* added to 200 µg Chemagen beads coated with Carrageenan
Well no 4=100 µl $10^{-3}$ dilution of *E. coli* added to 200 µg Chemagen beads coated with Carrageenan
Well no 5=100 µl $10^{-4}$ dilution of *E. coli* added to 200 µg Chemagen beads coated with Carrageenan
Well no 6=100 µl $10^{-5}$ dilution of *E. coli* added to 200 µg Chemagen beads coated with Carrageenan
Well no 7=100 µl $10^{-6}$ dilution of *E. coli* added to 200 µg Chemagen beads coated with Carrageenan
Well no 8=100 µl $10^{-7}$ dilution of *E. coli* added to 200 µg Chemagen beads coated with Carrageenan
Well no 9=negative control
Line 2:
Well no 1=Hae III marker
Well no 2=100 µl $10^{-1}$ dilution of *E. coli* added to 200 µg Chemagen beads coated with Mannose
Well no 3=100 µl $10^{-2}$ dilution of *E. coli* added to 200 µg Chemagen beads coated with Mannose
Well no 4=100 µl $10^{-3}$ dilution of *E. coli* added to 200 µg Chemagen beads coated with Mannose
Well no 5=100 µl $10^{-4}$ dilution of *E. coli* added to 200 µg Chemagen beads coated with Mannose
Well no 6=100 µl $10^{-5}$ dilution of *E. coli* added to 200 µg Chemagen beads coated with Mannose
Well no 7=100 µl $10^{-6}$ dilution of *E. coli* added to 200 µg Chemagen beads coated with Mannose
Well no 8=100 µl $10^{-7}$ dilution of *E. coli* added to 200 µg Chemagen beads coated with Mannose
Line 3:
Well no 1=Hae III marker
Well no 2=100 µl $10^{-1}$ dilution of *E. coli* added to 200 µg Chemagen beads coated with Gum
Well no 3=100 µl $10^{-2}$ dilution of *E. coli* added to 200 µg Chemagen beads coated with Gum
Well no 4=100 µl $10^{-3}$ dilution of *E. coli* added to 200 µg Chemagen beads coated with Gum
Well no 5=100 µl $10^{-4}$ dilution of *E. coli* added to 200 µg Chemagen beads coated with Gum
Well no 6=100 µl $10^{-5}$ dilution of *E. coli* added to 200 µg Chemagen beads coated with Gum
Well no 7=100 µl $10^{-6}$ dilution of *E. coli* added to 200 µg Chemagen beads coated with Gum
Well no 8=100 µl $10^{-7}$ dilution of *E. coli* added to 200 µg Chemagen beads coated with Gum
Line 4:
Well no 1=Hae III marker
Well no 2=100 µl $10^{-1}$ dilution of *E. coli* added to 200 µg Dynabeads coated with Mannan
Well no 3=100 µl $10^{-2}$ dilution of *E. coli* added to 200 µg Dynabeads coated with Mannan
Well no 4=100 µl $10^{-3}$ dilution of *E. coli* added to 200 µg Dynabeads coated with Mannan
Well no 5=100 µl $10^{-4}$ dilution of *E. coli* added to 200 µg Dynabeads coated with Mannan
Well no 6=100 µl $10^{-5}$ dilution of *E. coli* added to 200 µg Dynabeads coated with Mannan
Well no 7=100 µl $10^{-6}$ dilution of *E. coli* added to 200 µg Dynabeads coated with Mannan
Well no 8=100 µl $10^{-7}$ dilution of *E. coli* added to 200 µg Dynabeads coated with Mannan
Line 5:
Well no 1=Hae III marker
Well no 2=100 µl $10^{-1}$ dilution of *E. coli* added to 200 µg Dynabeads coated with Mannose
Well no 3=100 µl $10^{-2}$ dilution of *E. coli* added to 200 µg Dynabeads coated with Mannose
Well no 4=100 µl $10^{-3}$ dilution of *E. coli* added to 200 µg Dynabeads coated with Mannose
Well no 5=100 µl $10^{-4}$ dilution of *E. coli* added to 200 µg Dynabeads coated with Mannose
Well no 6=100 µl $10^{-5}$ dilution of *E. coli* added to 200 µg Dynabeads coated with Mannose
Well no 7=100 µl $10^{-6}$ dilution of *E. coli* added to 200 µg Dynabeads coated with Mannose
Well no 8=100 µl $10^{-7}$ dilution of *E. coli* added to 200 µg Dynabeads coated with Mannose
Line 6:
Well no 1=Hae III marker
Well no 2=100 µl $10^{-1}$ dilution of *E. coli* added to 200 µg Dynabeads coated with Gum
Well no 3=100 µl $10^{-2}$ dilution of *E. coli* added to 200 µg Dynabeads coated with Gum
Well no 4=100 µl $10^{-3}$ dilution of *E. coli* added to 200 µg Dynabeads coated with Gum
Well no 5=100 µl $10^{-4}$ dilution of *E. coli* added to 200 µg Dynabeads coated with Gum Well no 6=100 µl $10^{-5}$ dilution of E. coli added to 200 µg Dynabeads coated with Gum
Well no 7=100 µl $10^{-6}$ dilution of E. coli added to 200 µg Dynabeads coated with Gum
Well no 8=100 µl $10^{-1}$ dilution of E. coli added to 200 µg Dynabeads coated with Gum D. Isolation of Genomic DNA from *Salmonella typhimurium* Using Carrageenan, Mannose, Gum, Mannan The results of amplification are shown in the gel photograph of FIG. 7.

Reading from the top left side on the gel:

Line 1:
Well no 1=Hae III marker
Well no 2=100 µl $10^{-1}$ dilution of S. typhimurium added to 200 µg Chemagen beads coated with Carrageenan
Well no 3=100 µl $10^{-2}$ dilution of S. typhimurium added to 200 µg Chemagen beads coated with Carrageenan
Well no 4=100 µl $10^{-3}$ dilution of S. typhimurium added to 200 µg Chemagen beads coated with Carrageenan
Well no 5=100 µl $10^{-4}$ dilution of S. typhimurium added to 200 µg Chemagen beads coated with Carrageenan
Well no 6=100 µl $10^{-5}$ dilution of S. typhimurium added to 200 µg Chemagen beads coated with Carrageenan
Well no 7=100 µl $10^{-6}$ dilution of S. typhimurium added to 200 µg Chemagen beads coated with Carrageenan
Well no 8=100 µl $10^{-7}$ dilution of S. typhimurium added to 200 µg Chemagen beads coated with Carrageenan
Well no 9=negative control Line 2:
Well no 1=Hae III marker
Well no 2=100 µl $10^{-1}$ dilution of S. typhimurium added to 200 µg Chemagen beads coated with Mannose
Well no 3=100 µl $10^{-2}$ dilution of S. typhimurium added to 200 µg Chemagen beads coated with Mannose
Well no 4=100 µl $10^{-3}$ dilution of S. typhimurium added to 200 µg Chemagen beads coated with Mannose
Well no 5=100 µl $10^{-4}$ dilution of S. typhimurium added to 200 µg Chemagen beads coated with Mannose
Well no 6=100 µl $10^{-5}$ dilution of S. typhimurium added to 200 µg Chemagen beads coated with Mannose
Well no 7=100 µl $10^{-6}$ dilution of S. typhimurium added to 200 µg Chemagen beads coated with Mannose
Well no 8=100 µl $10^{-7}$ dilution of S. typhimurium added to 200 µg Chemagen beads coated with Mannose Line 3:
Well no 1=Hae III marker
Well no 2=100 µl $10^{-1}$ dilution of S. typhimurium added to 200 µg Chemagen beads coated with Gum
Well no 3=100 µl $10^{-2}$ dilution of S. typhimurium added to 200 µg Chemagen beads coated with Gum
Well no 4=100 µl $10^{-3}$ dilution of S. typhimurium added to 200 µg Chemagen beads coated with Gum
Well no 5=100 µl $10^{-4}$ dilution of S. typhimurium added to 200 µg Chemagen beads coated with Gum
Well no 6=100 µl $10^{-5}$ dilution of S. typhimurium added to 200 µg Chemagen beads coated with Gum
Well no 7=100 µl $10^{-6}$ dilution of S. typhimurium added to 200 µg Chemagen beads coated with Gum
Well no 8=100 µl $10^{-7}$ dilution of S. typhimurium added to 200 µg Chemagen beads coated with Gum Line 4:
Well no 1=Hae III marker
Well no 2=100 µl $10^{-1}$ dilution of S. typhimurium added to 200 µg Dynabeads coated with Mannan
Well no 3=100 µl $10^{-2}$ dilution of S. typhimurium added to 200 µg Dynabeads coated with Mannan
Well no 4=100 µl $10^{-3}$ dilution of S. typhimurium added to 200 µg Dynabeads coated with Mannan
Well no 5=100 µl $10^{-4}$ dilution of S. typhimurium added to 200 µg Dynabeads coated with Mannan
Well no 6=100 µl $10^{-5}$ dilution of S. typhimurium added to 200 µg Dynabeads coated with Mannan
Well no 7=100 µl $10^{-6}$ dilution of S. typhimurium added to 200 µg Dynabeads coated with Mannan
Well no 8=100 µl $10^{-7}$ dilution of S. typhimurium added to 200 µg Dynabeads coated with Mannan Line 5:
Well no 1=Hae III marker
Well no 2=100 µl $10^{-1}$ dilution of S. typhimurium added to 200 µg Dynabeads coated with Mannose
Well no 3=100 µl $10^{-2}$ dilution of S. typhimurium added to 200 µg Dynabeads coated with Mannose
Well no 4=100 µl $10^{-3}$ dilution of S. typhimurium added to 200 µg Dynabeads coated with Mannose
Well no 5=100 µl $10^{-4}$ dilution of S. typhimurium added to 200 µg Dynabeads coated with Mannose
Well no 6=100 µl $10^{-5}$ dilution of S. typhimurium added to 200 µg Dynabeads coated with Mannose
Well no 7=100 µl $10^{-6}$ dilution of S. typhimurium added to 200 µg Dynabeads coated with Mannose
Well no 8=100 µl $10^{-7}$ dilution of S. typhimurium added to 200 µg Dynabeads coated with Mannose Line 6:
Well no 1=Hae III marker
Well no 2=100 µl $10^{-1}$ dilution of S. typhimurium added to 200 µg Dynabeads coated with Gum
Well no 3=100 µl $10^{-2}$ dilution of S. typhimurium added to 200 µg Dynabeads coated with Gum
Well no 4=100 µl $10^{-3}$ dilution of S. typhimurium added to 200 µg Dynabeads coated with Gum
Well no 5=100 µl $10^{-4}$ dilution of S. typhimurium added to 200 µg Dynabeads coated with Gum
Well no 6=100 µl $10^{-5}$ dilution of S. typhimurium added to 200 µg Dynabeads coated with Gum
Well no 7=100 µl $10^{-6}$ dilution of S. typhimurium added to 200 µg Dynabeads coated with Gum
Well no 8=100 µl $10^{-7}$ dilution of S. typhimurium added to 200 µg Dynabeads coated with Gum Isolation of DNA from *Salmonella typhimurium*

Figure 8:
FIG. 8 is a photograph of a gel showing PCR products from the nucleic acid of *Campylobacter jejuni* bound to various coated beads.

E. Isolation of DNA from *Campylobacter jejuni* Using Guar, Gum, Mannose & Carrageenan The results of amplification are shown in the gel photograph of FIG. 8.

Figure 9:
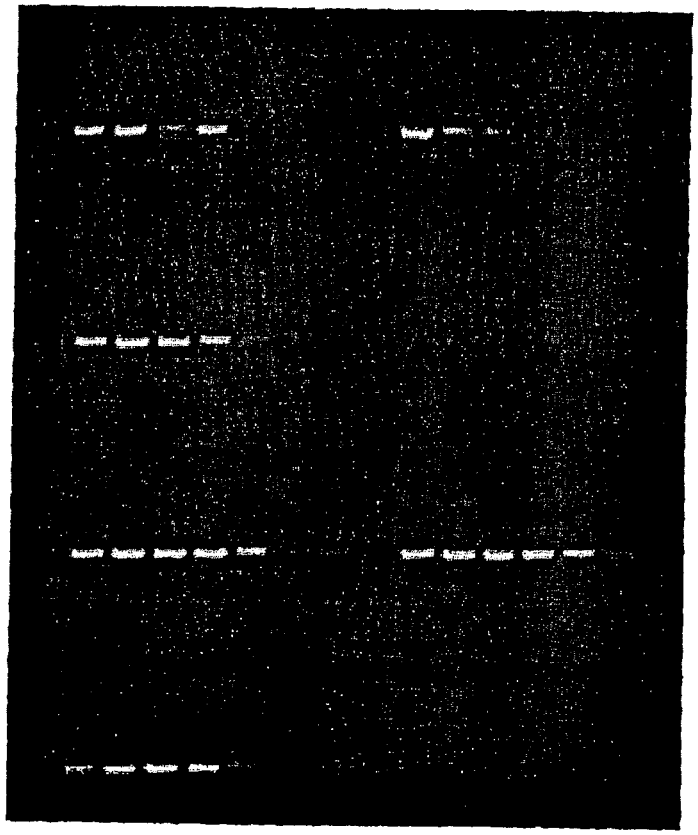
FIG. 9 is a photograph of a gel showing PCR products from the nucleic acid of *Steptococcus pyogenes* bound to various coated beads.

Well no 1=Hae III marker
Well no 2=100 µl $10^{-1}$ dilution of C. jejuni added to 200 µg Dynabeads coated with Guar
Well no 3=100 µl $10^{-2}$ dilution of C. jejuni added to 200 µg Dynabeads coated with Guar
Well no 4=100 µl $10^{-3}$ dilution of C. jejuni added to 200 µg Dynabeads coated with Guar
Well no 5=100 µl $10^{-4}$ dilution of C. jejuni added to 200 µg Dynabeads coated with Guar
Well no 6=100 µl $10^{-5}$ dilution of C. jejuni added to 200 µg Dynabeads coated with Guar
Well no 7=100 µl $10^{-6}$ dilution of C. jejuni added to 200 µg Dynabeads coated with Guar
Well no 8=100 µl $10^{-1}$ dilution of C. jejuni added to 200 µg Dynabeads coated with Gum
Well no 9=100 µl $10^{-2}$ dilution of C. jejuni added to 200 µg Dynabeads coated with Gum
Well no 10=100 µl $10^{-3}$ dilution of C. jejuni added to 200 µg Dynabeads coated with Gum Well no 11=100 µl $10^{-4}$ dilution of *C. jejuni* added to 200 µg Dynabeads coated with Gum
Well no 12=100 µl $10^{-5}$ dilution of *C. jejuni* added to 200 µg Dynabeads coated with Gum
Well no 13=100 µl $10^{-6}$ dilution of *C. jejuni* added to 200 µg Dynabeads coated with Gum
Well no 14=100 µl $10^{-1}$ dilution of *C. jejuni* added to 200 µg Dynabeads coated with Mannose
Well no 15=100 µl $10^{-2}$ dilution of *C. jejuni* added to 200 µg Dynabeads coated with Mannose
Well no 16=100 µl $10^{-3}$ dilution of *C. jejuni* added to 200 µg Dynabeads coated with Mannose
Well no 17=100 µl $10^{-4}$ dilution of *C. jejuni* added to 200 µg Dynabeads coated with Mannose
Well no 18=100 µl $10^{-5}$ dilution of *C. jejuni* added to 200 µg Dynabeads coated with Mannose
Well no 19=100 µl $10^{-6}$ dilution of *C. jejuni* added to 200 µg Dynabeads coated with Mannose
Well no 20=100 µl $10^{-1}$ dilution of *C. jejuni* added to 200 µg Chemagen beads coated with Mannose
Well no 21=100 µl $10^{-2}$ dilution of *C. jejuni* added to 200 µg Chemagen beads coated with Mannose
Well no 22=100 µl $10^{-3}$ dilution of *C. jejuni* added to 200 µg Chemagen beads coated with Mannose
Well no 23=100 µl $10^{-4}$ dilution of *C. jejuni* added to 200 µg Chemagen beads coated with Mannose
Well no 24=100 µl $10^{-5}$ dilution of *C. jejuni* added to 200 µg Chemagen beads coated with Mannose
Well no 25=100 µl $10^{-6}$ dilution of *C. jejuni* added to 200 µg Chemagen beads coated with Mannose
Well no 26=100 µl $10^{-1}$ dilution of *C. jejuni* added to 200 µg Chemagen beads coated with Gum
Well no 27=100 µl $10^{-2}$ dilution of *C. jejuni* added to 200 µg Chemagen beads coated with Gum
Well no 28=100 µl $10^{-3}$ dilution of *C. jejuni* added to 200 µg Chemagen beads coated with Gum
Well no 29=100 µl $10^{-4}$ dilution of *C. jejuni* added to 200 µg Chemagen beads coated with Gum
Well no 30=100 µl $10^{-5}$ dilution of *C. jejuni* added to 200 µg Chemagen beads coated with Gum
Well no 31=100 µl $10^{-6}$ dilution of *C. jejuni* added to 200 µg Chemagen beads coated with Gum
Well no 32=100 µl $10^{-1}$ dilution of *C. jejuni* added to 200 µg Chemagen beads coated with Carrageenan
Well no 33=100 µl $10^{-2}$ dilution of *C. jejuni* added to 200 µg Chemagen beads coated with Carrageenan
Well no 34=100 µl $10^{-3}$ dilution of *C. jejuni* added to 200 µChemagen beads coated with Carrageenan
Well no 35=100 µl $10^{-4}$ dilution of *C. jejuni* added to 200 µg Chemagen beads coated with Carrageenan
Well no 36=100 µl $10^{-5}$ dilution of *C. jejuni* added to 200 µg Chemagen beads coated with Carrageenan
Well no 37=100 µl $10^{-6}$ dilution of *C. jejuni* added to 200 µg Chemagen beads coated with Carrageenan F. Isolation of Genomic DNA Form *Streptococcus pyogenes* Using Gum, Heparin, Carrageenan & Dextran Sulphate The results of amplification are shown in the gel photograph of FIG. 9.

Figure 10:
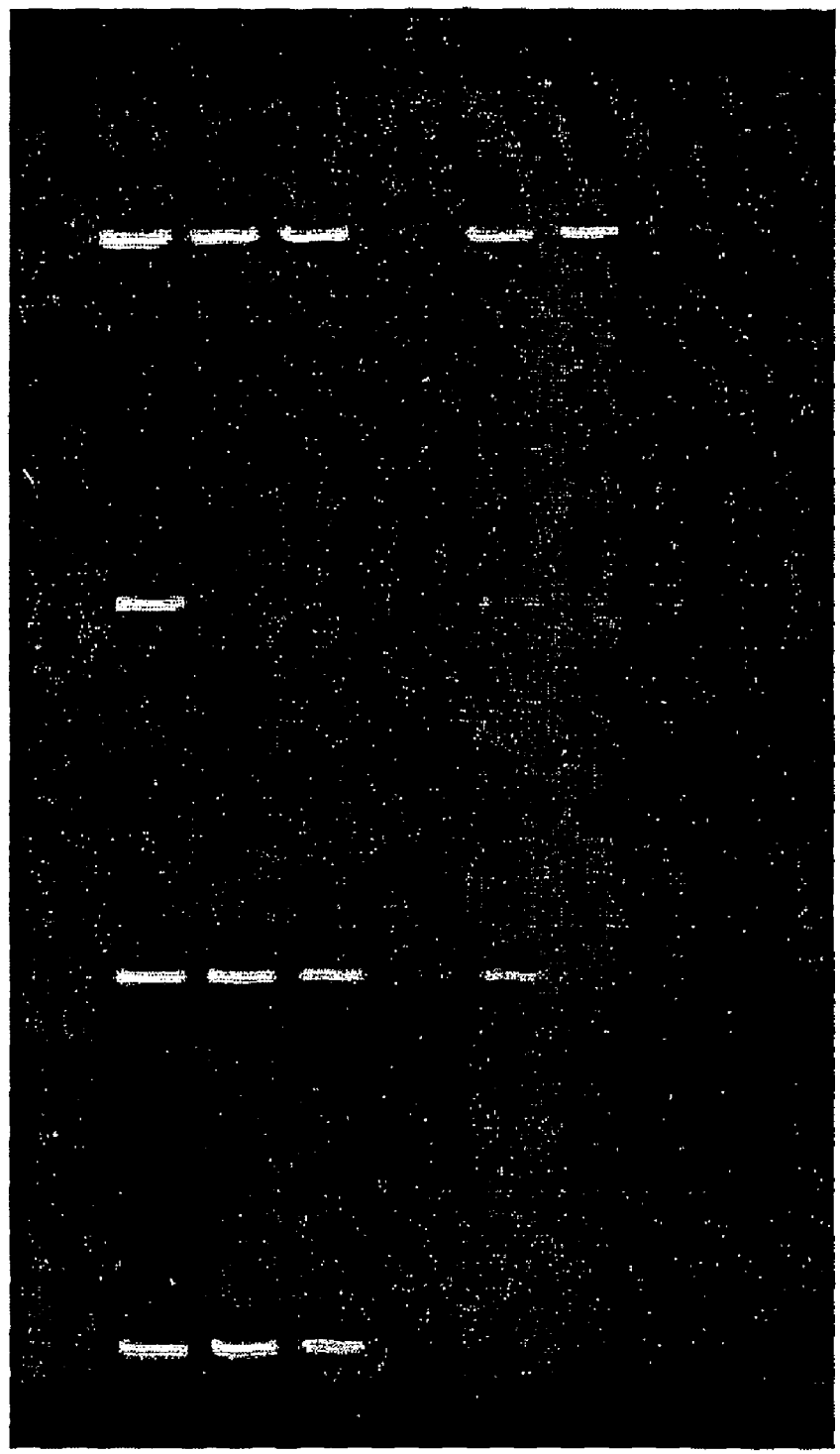
FIG. 10 is a photograph of a gel showing PCR products from the nucleic acid of *Neisseria gonorrheae* bound to various coated beads.

Line 1:
PCR performed on supernatant, separated from the beads with a magnet after incubation at 90° C. for 5 min.
Well no 1=Hae III marker
Well no 2=100 µl $10^{-1}$ dilution of *S. pyogenes* added to 200 µg Chemagen beads coated with Gum
Well no 3=100 µl $10^{-2}$ dilution of *S. pyogenes* added to 200 µg Chemagen beads coated with Gum
Well no 4=100 µl $10^{-3}$ dilution of *S. pyogenes* added to 200 µg Chemagen beads coated with Gum
Well no 5=100 µl $10^{-4}$ dilution of *S. pyogenes* added to 200 µg Chemagen beads coated with Gum
Well no 6=100 µl $10^{-5}$ dilution of *S. pyogenes* added to 200 µg Chemagen beads coated with Gum
Well no 7=100 µl $10^{-6}$ dilution of *S. pyogenes* added to 200 µg Chemagen beads coated with Gum
Well no 8=100 µl $10^{-6}$ dilution of *S. pyogenes* added to 200 µg Chemagen beads coated with Gum
Well no 9=100 µl $10^{-6}$ dilution of *S. pyogenes* added to 200 µg Chemagen beads coated with Gum
PCR run on the rest of the beads after resuspension in water
Well no 10=100 µl $10^{-1}$ dilution of *S. pyogenes* added to 200 µg Chemagen beads coated with Gum
Well no 11=100 µl $10^{-2}$ dilution of *S. pyogenes* added to 200 µg Chemagen beads coated with Gum
Well no 12=100 µl $10^{-1}$ dilution of *S. pyogenes* added to 200 µg Chemagen beads coated with Gum
Well no 13=100 µl $10^{-4}$ dilution of *S. pyogenes* added to 200 µg Chemagen beads coated with Gum
Well no 14=100 µl $10^{-5}$ dilution of *S. pyogenes* added to 200 µg Chemagen beads coated with Gum
Well no 15=100 µl $10^{-6}$ dilution of *S. pyogenes* added to 200 µg Chemagen beads coated with Gum Line 2:
PCR performed on supernatant, separated from the beads with a magnet after incubation at 90° C. for 5 min.
Well no 1=Hae III marker
Well no 2=100 µl $10^{-1}$ dilution of *S. pyogenes* added to 200 µg Chemagen beads coated with Heparin
Well no 3=100 µl $10^{-2}$ dilution of *S. pyogenes* added to 200 µg Chemagen beads coated with Heparin
Well no 4=100 µl $10^{-3}$ dilution of *S. pyogenes* added to 200 µg Chemagen beads coated with Heparin
Well no 5=100 µl $10^{-4}$ dilution of *S. pyogenes* added to 200 µg Chemagen beads coated with Heparin
Well no 6=100 µl $10^{-5}$ dilution of *S. pyogenes* added to 200 µg Chemagen beads coated with Heparin
Well no 7=100 µl $10^{-6}$ dilution of *S. pyogenes* added to 200 µg Chemagen beads coated with Heparin
Well no 8=100 µl $10^{-6}$ dilution of *S. pyogenes* added to 200 µg Chemagen beads coated with Heparin
Well no 9=100 µl $10^{-6}$ dilution of *S. pyogenes* added to 200 µg Chemagen beads coated with Heparin
PCR run on the rest of the beads after resuspension in water
Well no 10=100 µl $10^{-1}$ dilution of *S. pyogenes* added to 200 µg Chemagen beads coated with Heparin
Well no 11=100 µl $10^{-2}$ dilution of *S. pyogenes* added to 200 µg Chemagen beads coated with Heparin
Well no 12=100 µl $10^{-3}$ dilution of *S. pyogenes* added to 200 µg Chemagen beads coated with Heparin
Well no 13=100 µl $10^{-4}$ dilution of *S. pyogenes* added to 200 µg Chemagen beads coated with Heparin
Well no 14=100 µl $10^{-5}$ dilution of *S. pyogenes* added to 200 µg Chemagen beads coated with Heparin
Well no 15=100 µl $10^{-6}$ dilution of *S. pyogenes* added to 200 µg Chemagen beads coated with Heparin Line 3:
PCR performed on supernatant, separated from the beads with a magnet after incubation at 90° C. for 5 min.
Well no 1=Hae III marker
Well no 2=100 µl $10^{-1}$ dilution of *S. pyogenes* added to 200 µg Chemagen beads coated with Carrageenan
Well no 3=100 µl $10^{-2}$ dilution of *S. pyogenes* added to 200 µg Chemagen beads coated with Carrageenan Well no 4=100 µl $10^{-3}$ dilution of *S. pyogenes* added to 200 µg Chemagen beads coated with Carrageenan
Well no 5=100 µl $10^{-4}$ dilution of *S. pyogenes* added to 200 µg Chemagen beads coated with Carrageenan
Well no 6=100 µl $10^{-5}$ dilution of *S. pyogenes* added to 200 µg Chemagen beads coated with Carrageenan
Well no 7=100 µl $10^{-6}$ dilution of *S. pyogenes* added to 200 µg Chemagen beads coated with Carrageenan
Well no 8=100 µl $10^{-6}$ dilution of *S. pyogenes* added to 200 µg Chemagen beads coated with Carrageenan
Well no 9=100 µl $10^{-6}$ dilution of *S. pyogenes* added to 200 µg Chemagen beads coated with Carrageenan
PCR run on the rest of the beads after resuspension in water
Well no 10=100 µl $10^{-1}$ dilution of *S. pyogenes* added to 200 µg Chemagen beads coated with Carrageenan
Well no 11=100 µl $10^{-2}$ dilution of *S. pyogenes* added to 200 µg Chemagen beads coated with Carrageenan
Well no 12=100 µl $10^{-3}$ dilution of *S. pyogenes* added to 200 µg Chemagen beads coated with Carrageenan
Well no 13=100 µl $10^{-4}$ dilution of *S. pyogenes* added to 200 µg Chemagen beads coated with Carrageenan
Well no 14=100 µl $10^{-5}$ dilution of *S. pyogenes* added to 200 µg Chemagen beads coated with Carrageenan
Well no 15=100 µl $10^{-6}$ dilution of *S. pyogenes* added to 200 µg Chemagen beads coated with Carrageenan
Line 4:
PCR performed on supernatant, separated from the beads with a magnet after incubation at 90° C. for 5 min.
Well no 1=Hae III marker
Well no 2=100 µl $10^{-1}$ dilution of *S. pyogenes* added to 200 µg Chemagen beads coated with Dextran sulphate
Well no 3=100 µl $10^{-2}$ dilution of *S. pyogenes* added to 200 µg Chemagen beads coated with Dextran sulphate
Well no 4=100 µl $10^{-3}$ dilution of *S. pyogenes* added to 200 µg Chemagen beads coated with Dextran sulphate
Well no 5=100 µl $10^{-4}$ dilution of *S. pyogenes* added to 200 µg Chemagen beads coated with Dextran sulphate
Well no 6=100 µl $10^{-5}$ dilution of *S. pyogenes* added to 200 µg Chemagen beads coated with Dextran sulphate
Well no 7=100 µl $10^{-6}$ dilution of *S. pyogenes* added to 200 µg Chemagen beads coated with Dextran sulphate
Well no 8=100 µl $10^{-6}$ dilution of *S. pyogenes* added to 200 µg Chemagen beads coated with Dextran sulphate
Well no 9=100 µl $10^{-6}$ dilution of *S. pyogenes* added to 200 µg Chemagen beads coated with Dextran sulphate
PCR run on the rest of the beads after resuspension in water
Well no 10=100 µl $10^{-1}$ dilution of *S. pyogenes* added to 200 µg Chemagen beads coated with Dextran sulphate
Well no 11=100 µl $10^{-2}$ dilution of *S. pyogenes* added to 200 µg Chemagen beads coated with Dextran sulphate
Well no 12=100 µl $10^{-3}$ dilution of *S. pyogenes* added to 200 µg Chemagen beads coated with Dextran sulphate
Well no 13=100 µl $10^{-4}$ dilution of *S. pyogenes* added to 200 µg Chemagen beads coated with Dextran sulphate
Well no 14=100 µl $10^{-5}$ dilution of *S. pyogenes* added to 200 µg Chemagen beads coated with Dextran sulphate
Well no 15=100 µl $10^{-6}$ dilution of *S. pyogenes* added to 200 µg Chemagen beads coated with Dextran sulphate G. Isolation of Genomic DNA from *Neisseria gonorrhoeae* Using Gum, Heparin, Carrageenan & Dextran Sulphate The results of amplification are shown in the gel photograph of FIG. 10.
Line 1:
PCR performed on supernatant, separated from the beads with a magnet after incubation at 90° C. for 5 min.
Well no 1=Hae III marker
Well no 2=100 µl $10^{-1}$ dilution of *N. gonorrhoeae* added to 200 µg Chemagen beads coated with Gum
Well no 3=100 µl $10^{-2}$ dilution of *N. gonorrhoeae* added to 200 µg Chemagen beads coated with Gum
Well no 4=100 µl $10^{-3}$ dilution of *N. gonorrhoeae* added to 200 µg Chemagen beads coated with Gum
Well no 5=100 µl $10^{-4}$ dilution of *N. gonorrhoeae* added to 200 µg Chemagen beads coated with Gum
PCR run on the rest of the beads after resuspension in water
Well no 6=100 µl $10^{-5}$ dilution of *N. gonorrhoeae* added to 200 µg Chemagen beads coated with Gum
Well no 7=100 µl $10^{-6}$ dilution of *N. gonorrhoeae* added to 200 µg Chemagen beads coated with Gum
Well no 8=100 µl $10^{-6}$ dilution of *N. gonorrhoeae* added to 200 µg Chemagen beads coated with Gum
Well no 9=100 µl $10^{-6}$ dilution of *N. gonorrhoeae* added to 200 µg Chemagen beads coated with Gum
Line 2:
PCR performed on supernatant, separated from the beads with a magnet after incubation at 90° C. for 5 min.
Well no 1=Hae III marker
Well no 2=100 µl $10^{-1}$ dilution of *N. gonorrhoeae* added to 200 µg Chemagen beads coated with Heparin
Well no 3=100 µl $10^{-2}$ dilution of *N. gonorrhoeae* added to 200 µg Chemagen beads coated with Heparin
Well no 4=100 µl $10^{-3}$ dilution of *N. gonorrhoeae* added to 200 µg Chemagen beads coated with Heparin
Well no 5=100 µl $10^{-4}$ dilution of *N. gonorrhoeae* added to 200 µg Chemagen beads coated with Heparin
PCR run on the rest of the beads after resuspension in water
Well no 6=100 µl $10^{-5}$ dilution of *N. gonorrhoeae* added to 200 µg Chemagen beads coated with Heparin
Well no 7=100 µl $10^{-6}$ dilution of *N. gonorrhoeae* added to 200 µg Chemagen beads coated with Heparin
Well no 8=100 µl $10^{-6}$ dilution of *N. gonorrhoeae* added to 200 µg Chemagen beads coated with Heparin
Well no 9=100 µl $10^{-6}$ dilution of *N. gonorrhoeae* added to 200 µg Chemagen beads coated with Heparin
Line 3:
PCR performed on supernatant, separated from the beads with a magnet after incubation at 90° C. for 5 min.
Well no 1=Hae III marker
Well no 2=100 µl $10^{-1}$ dilution of *N. gonorrhoeae* added to 200 µg Chemagen beads coated with Carrageenan
Well no 3=100 µl $10^{-2}$ dilution of *N. gonorrhoeae* added to 200 µg Chemagen beads coated with Carrageenan
Well no 4=100 µl $10^{-3}$ dilution of *N. gonorrhoeae* added to 200 µg Chemagen beads coated with Carrageenan
Well no 5=100 µl $10^{-4}$ dilution of *N. gonorrhoeae* added to 200 µg Chemagen beads coated with Carrageenan
PCR run on the rest of the beads after resuspension in water
Well no 6=100 µl $10^{-5}$ dilution of *N. gonorrhoeae* added to 200 µg Chemagen beads coated with Carrageenan
Well no 7=100 µl $10^{-6}$ dilution of *N. gonorrhoeae* added to 200 µg Chemagen beads coated with Carrageenan
Well no 8=100 µl $10^{-6}$ dilution of *N. gonorrhoeae* added to 200 µg Chemagen beads coated with Carrageenan
Well no 9=100 µl $10^{-6}$ dilution of *N. gonorrhoeae* added to 200 µg Chemagen beads coated with Carrageenan
Line 4:
PCR performed on supernatant, separated from the beads with a magnet after incubation at 90° C. for 5 min.
Well no 1=Hae III marker
Well no 2=100 µl $10^{-1}$ dilution of *N. gonorrhoeae* added to 200 µg Chemagen beads coated with Dextran sulphate Well no 3=100 μl $10^{-2}$ dilution of *N. gonorrhoeae* added to 200 μg Chemagen beads coated with Dextran sulphate
Well no 4=100 μl $10^{-3}$ dilution of *N. gonorrhoeae* added to 200 μg Chemagen beads coated with Dextran sulphate
Well no 5=100 μl $10^{-4}$ dilution of *N. gonorrhoeae* added to 200 μg Chemagen beads coated with Dextran sulphate
PCR run on the rest of the beads after resuspension in water
Well no 6=100 μl $10^{-5}$ dilution of *N. gonorrhoeae* added to 200 μg Chemagen beads coated with Dextran sulphate
Well no 7=100 μl $10^{-6}$ dilution of *N. gonorrhoeae* added to 200 μg Chemagen beads coated with Dextran sulphate
Well no 8=100 μl $10^{-6}$ dilution of *N. gonorrhoeae* added to 200 μg Chemagen beads coated with Dextran sulphate
Well no 9=100 μl $10^{-6}$ dilution of *N. gonorrhoeae* added to 200 μg Chemagen beads coated with Dextran sulphate

EXAMPLE 11

The experiment was performed on pure culture of cancer B-cell line called J558L. The primers used were:

```
UPPER:     5' CCCGCCCCTTGCCTCTC 3'
LOWER:     5' TGGTCGCTCGCTCCTCTC 3'
```

Figure 11:
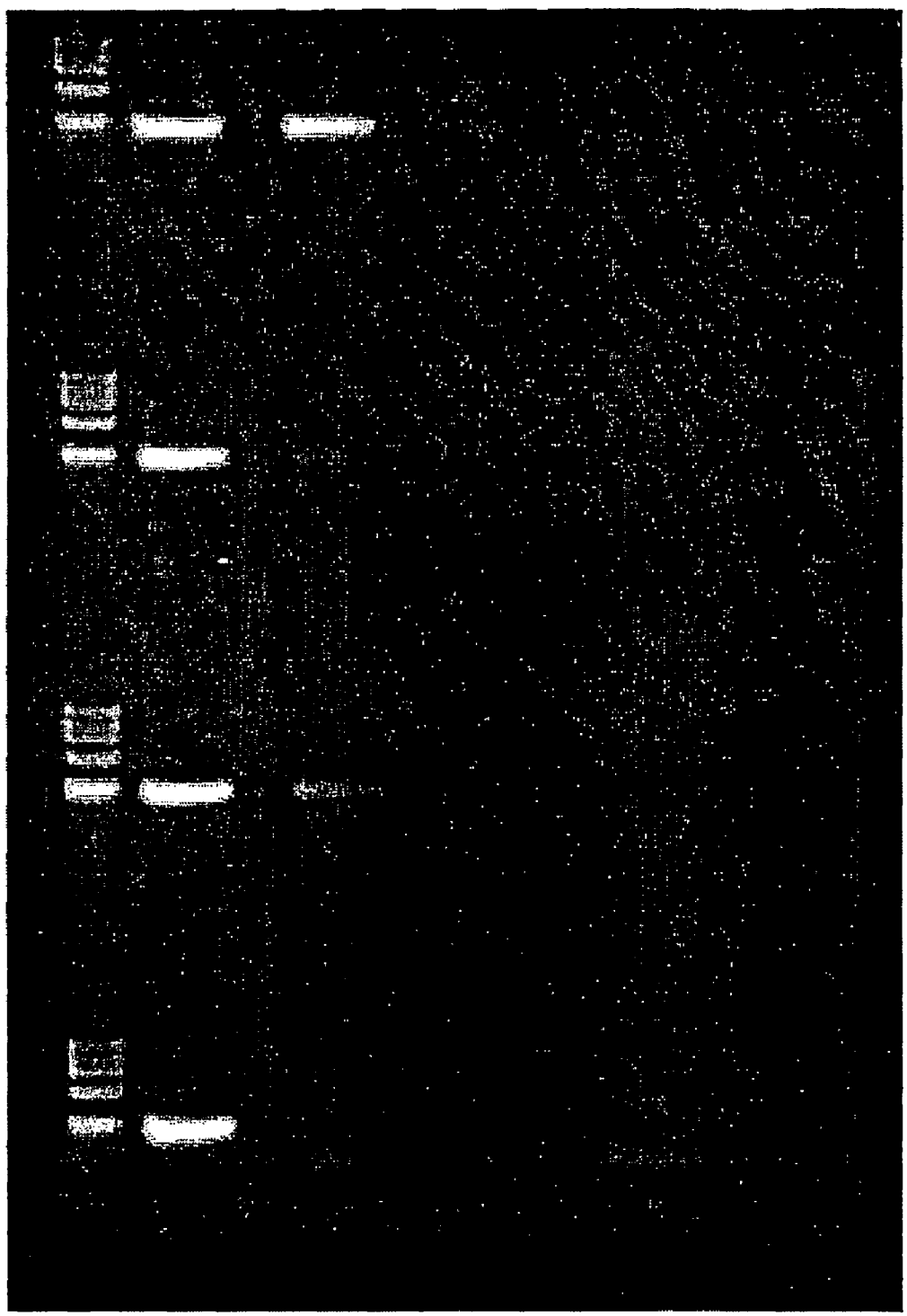
FIG. 11 is a photograph of a gel showing PCR products from the nucleic acid of human white blood cells bound to various coated beads.

The results of amplification are shown in the gel photograph of FIG. 11. PCR was performed on the supernatant, separated from the beads with a magnet after incubation at 90° C. for 5 min.
Line 1:
Well no. 1=Hae III marker
Well no. 2=100 μl $10^{-0}$ dilution of B-cells added to 200 μg chemagen beads coated with Type V carrageenan.
Well no. 3=100 μl $10^{-1}$ dilution of B-cells added to 200 μg chemagens beads coated with Type V carrageenan
Well no. 4=100 μl $10^{-2}$ dilution of B-cells added to 200 μg chemagens beads coated with Type V carrageenan
Well no. 5=100 μl $10^{-3}$ dilution of B-cells added to 200 μg chemagen beads coated with Type V carrageenan
Line 2:
Well no. 1=Hae III marker
Well no. 2=100 μl $10^{-0}$ dilution of B-cells added to 200 μg Dynabeads coated with Type I carrageenan.
Well no. 3=100 μl $10^{-1}$ dilution of B-cells added to 200 μg Dynabeads coated with Type I carrageenan
Well no. 4=100 μl $10^{-2}$ dilution of B-cells added to 200 μg Dynabeads coated with Type I carrageenan
Well no. 5=100 μl $10^{-3}$ dilution of B-cells added to 200 μg Dynabeads coated with Type I carrageenan
Line 3:
Well no. 1=Hae III marker
Well no. 2=100 μl $10^{-0}$ dilution of B-cells added to 200 μg Dynabeads coated with Type II carrageenan.
Well no. 3=100 μl $10^{-1}$ dilution of B-cells added to 200 μg Dynabeads coated with Type II carrageenan
Well no. 4=100 μl $10^{-2}$ dilution of B-cells added to 200 μg Dynabeads coated with Type II carrageenan
Well no. 5=100 μl $10^{-3}$ dilution of B-cells added to 200 μg Dynabeads coated with Type II carrageenan
Line 4:
Well no. 1=Hae III marker
Well no. 2=100 μl $10^{-}$ dilution of B-cells added to 200 μg Dynabeads coated with Type V carrageenan.
Well no. 3=100 μl $10^{-1}$ dilution of B-cells added to 200 μg Dynabeads coated with Type V carrageenan
Well no. 4=100 μl $10^{-2}$ dilution of B-cells added to 200 μg Dynabeads coated with Type V carrageenan
Well no. 5=100 μl $10^{-3}$ dilution of B-cells added to 200 μg Dynabeads coated with Type V carrageenan The various types of carrageenan used (with their product no. in Sigma catalog):
Type I carrageenan—mostly kappa carrageenan: C1013
Type II carrageenan—mostly iota carrageenan: C1138
Type V carrageenan—iota carrageenan: C-3889

EXAMPLE 12

Figure 12:
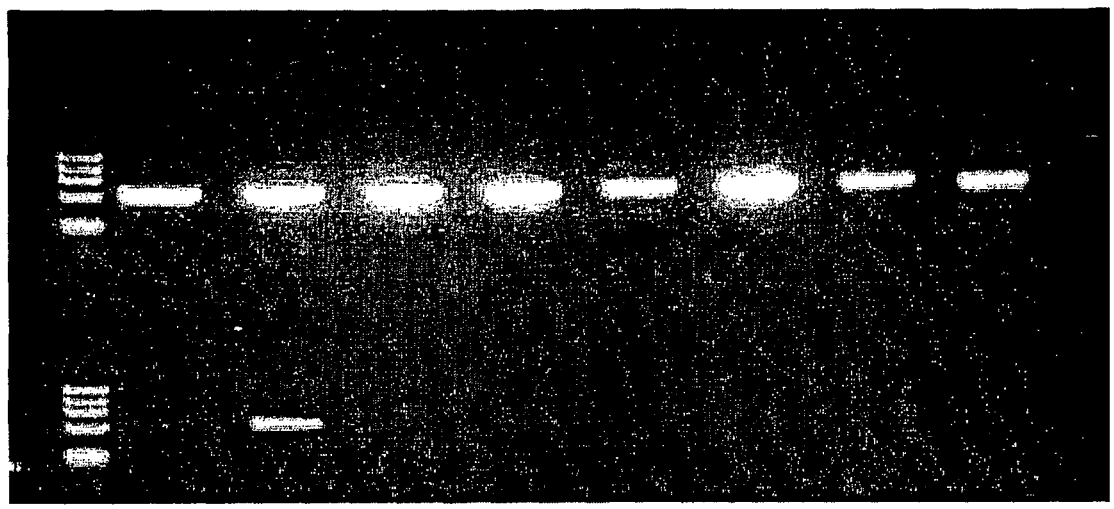
FIG. 12 is a photograph of a gel showing PCR products from the nucleic acid of *E. coli* bound to coated and uncoated Dynabeads.

*E. coli* was isolated from beads coated with GUM according to the protocol of Example 8. The uncoated beads went through the same coating procedure as the coated beads, but no sugar was added. The isolation protocol of Example 9 was followed according to the following dilutions:
Line 1:
Well no 1=Hae III marker
Well no 2=100 μl $10^{-1}$ dilution of *E. coli* added to 200 μg uncoated Dynabeads beads
Well no 3=100 μl $10^{-1}$ dilution of *E. coli* added to 200 μg Dynabeads beads coated with Gum
Well no 4=100 μl $10^{-2}$ dilution of *E. coli* added to 200 μg uncoated Dynabeads beads
Well no 5=100 μl $10^{-2}$ dilution of *E. coli* added to 200 μg Dynabeads beads coated with Gum
Well no 6=1100 μl $10^{-3}$ dilution of *E. coli* added to 200 μg uncoated Dynabeads beads
Well no 7=100 μl $10^{-3}$ dilution of *E. coli* added to 200 μg Dynabeads beads coated with Gum
Well no 8=100 μl $10^{-4}$ dilution of *E. coli* added to 200 μg uncoated Dynabeads beads
Well no 9=100 μl $10^{-4}$ dilution of *E. coli* added to 200 μg Dynabeads beads coated with Gum
Line 2:
Well no 1=Hae III marker
Well no 2=100 μl $10^{-5}$ dilution of *E. coli* added to 200 μg uncoated Dynabeads beads coated
Well no 3=100 μl $10^{-5}$ dilution of *E. coli* added to 200 μg Dynabeads beads coated with Gum
Well no 4=100 μl $10^{-6}$ dilution of *E. coli* added to 200 μg uncoated Dynabeads beads coated
Well no 5=100 μl $10^{-6}$ dilution of *E. coli* added to 200 μg Dynabeads beads coated with Gum
Well no 7=100 μl $10^{-7}$ dilution of *E. coli* added to 200 μg uncoated Dynabeads beads coated
Well no 8=100 μl $10^{-7}$ dilution of *E. coli* added to 200 μg Dynabeads beads coated with Gum The results of amplification are shown in the gel photograph of FIG. 12.

EXAMPLE 13

Figure 13:
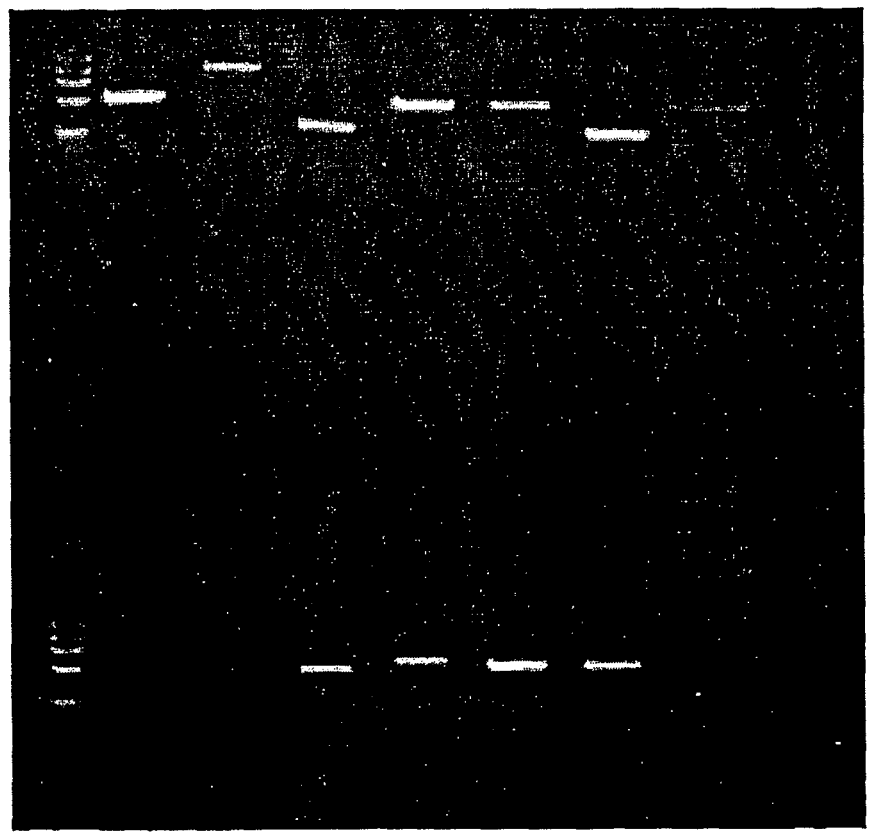
FIG. 13 is a photograph of a gel showing PCR products from nucleic acid of various bacteria bound to GUM coated Dynabeads.

Various bacterial species were isolated from beads coated with GUM according to the protocol of Example 8. The isolation protocol of Example 9 was followed and the results of amplification are shown in the gel photograph of FIG. 13 wherein:
Line 1:
Well no 1=Hae III marker
Well no 2=100 μl undiluted *Shigella flexneri* added to 200 μg Dynabeads coated with Gum
Well no 3=100 μl undiluted *Vibrio cholerae* added to 200 μg Dynabeads coated with Gum
Well no 4=100 μl undiluted *Aeromonas hydrophila* added to 200 μg Dynabeads coated with Gum
Well no 5=100 μl undiluted *Streptococcus pneumonia* added to 200 μg Dynabeads coated with Gum Well no. 5=100 μl $10^{-3}$ dilution of B-cells added to 200 μg Dynabeads coated with Type V carrageenan Well no 6=100 μl undiluted *Streptococcus pyogenes* added to 200 μg Dynabeads coated with Gum
Well no 7=100 μl undiluted *Salmonella typhimurium* added to 200 μg Dynabeads coated with Gum
Well no 8=100 μl undiluted *Yersinia enterocolitica* added to 200 μg Dynabeads coated with Gum
Line 2:
Well no 1=Hae III marker
Well no 2=100 μl undiluted *E. coli* added to 200 μg Dynabeads coated with Gum
Well no 3=100 μl undiluted *Listeria monocytogenes* added to 200 μg Dynabeads coated with Gum
Well no 4=100 μl undiluted *Clostridium perfringens* added to 200 μg Dynabeads coated with Gum
Well no 5=100 μl undiluted *Bacillus cereus* added to 200 μg Dynabeads coated with Gum
Well no 6=100 μl undiluted *Campylobacter jejuni* added to 200 μg Dynabeads coated with Gum.
Well no 7=100 μl undiluted *Neissseria gonorrhoeae* added to 200 μg Dynabeads coated with Gum
Well no 8=100 μl undiluted *Bordetella pertussis* added to 200 μg Dynabeads coated with Gum The primers for *bordetella* were the same as for *Nesseria* (see Table 1).

The invention claimed is:

1. A method of isolating cells from a sample which method comprises (a) binding said cells to a magnetic solid support by means of a non-specific ligand covalently attached to said solid support wherein said ligand is a polysaccharide comprising at least one of mannose, galactose and a derivative of mannose or galactose and wherein the cells bind to the saccharide moieties of said ligand; and (b) separating the solid support with the cells bound thereto from the remainder of the sample.

2. A method as claimed in claim 1 wherein the cells are microorganisms.

3. A method as claimed in claim 2 wherein the microorganisms are bacteria.

4. A method as claimed in claim 3 wherein representatives from at least 30% of the different bacterial species present in the sample are bound to said solid support.

5. A method as claimed in claim 3 wherein representatives from at least 60% of the different bacterial species present in the sample are bound to said solid support.

6. A method as claimed in claim 1 wherein the ligand is a nutrient.

7. A method as claimed in claim 1 wherein the ligand is selected from the group consisting of Gum, guar, carrageenan and mannan.

8. A method as claimed in claim 1 wherein the solid support is particulate.

9. A method as claimed in claim 1 which additionally comprises a step of identifying one or more of the cells bound to said solid support.

10. A method as claimed in claim 9 wherein the cells are identified using a cell type specific nucleic acid probe.

11. A method as claimed in claim 9 wherein the bound cells are lysed to release their nucleic acid.

12. A method as claimed in claim 11 wherein the released nucleic acid is bound to a solid support.

13. A method of detecting a microorganism in a sample, said method comprising:
 (a) binding said microorganism to a magnetic solid support by means of a non-specific ligand covalently attached to said solid support wherein said ligand is a polysaccharide comprising at least one of mannose, galactose and a derivative of mannose or galactose and wherein the cells bind to the saccharide moieties of said ligand;
 (b) separating the solid support with the cells bound thereto from the remainder of the sample; and
 (c) identifying the microorganism bound to said solid support.

14. A method as claimed in claim 13 wherein step (c) comprises lysing the microorganisms.

15. A method as claimed in claim 14 wherein the nucleic acid released from said lysed microorganisms is bound to a solid support.

16. The method as claimed in claim 1 wherein the derivative is selected from the group consisting of aldonic acid, uronic acid, deoxy, amino, sulfated and alcohol derivatives of galactose and mannose.

17. The method as claimed in claim 13 wherein the derivative is selected from the group consisting of aldonic acid, uronic acid, deoxy, amino, sulfated and alcohol derivatives of galactose and mannose.

18. The method as claimed in claim 1 wherein said ligand comprises 13 or more covalently linked monosaccharide units.

19. The method as claimed in claim 13 wherein said ligand comprises 13 or more covalently linked monosaccharide units.

20. A method as claimed in claim 1 wherein the ligand comprises mannose.

* * * * *